United States Patent [19]
Giese et al.

[11] Patent Number: 4,801,726
[45] Date of Patent: Jan. 31, 1989

[54] REPETITIVE HIT-AND-RUN IMMUNOASSAY AND STABLE SUPPORT-ANALYTE CONJUGATES; APPLIED TO T-2 TOXIN

[75] Inventors: Roger W. Giese, Quincy, Mass.; Beverly Warden, Nashua, N.H.; Allam Kariman, Dorchester, Mass.; Markus Ehrat, Suhr, Switzerland; Douglas J. Cecchini, Somerville; Abdellah Sentissi, West Roxbury, both of Mass.

[73] Assignee: Northeastern University, Boston, Mass.

[21] Appl. No.: 852,144

[22] Filed: Apr. 15, 1986

[51] Int. Cl.⁴ .............................................. C07F 7/10
[52] U.S. Cl. ..................................... 556/419; 556/421
[58] Field of Search .............................. 556/419, 421

[56] References Cited

U.S. PATENT DOCUMENTS

| | | | |
|---|---|---|---|
| 3,428,652 | 2/1969 | Sigg | 260/326.3 |
| 3,592,834 | 7/1971 | Buckman et al. | 556/419 X |
| 3,946,061 | 3/1976 | Buckman et al. | 556/419 X |
| 3,950,588 | 4/1976 | McDougal | 556/419 X |
| 4,244,874 | 1/1981 | Kaneko | 260/345.2 |
| 4,267,113 | 5/1981 | Kaneko et al. | 260/345.2 |
| 4,284,568 | 8/1981 | Schmitz et al. | 260/345.2 |
| 4,352,936 | 10/1982 | Kaneko | 549/332 |
| 4,413,134 | 11/1983 | Schmitz et al. | 549/332 |
| 4,415,665 | 11/1983 | Mosbach et al. | 435/179 |
| 4,433,158 | 2/1984 | Kaneko et al. | 549/332 |
| 4,434,236 | 2/1984 | Freytag | 436/512 |
| 4,446,232 | 5/1984 | Liotta | 435/7 |
| 4,456,765 | 6/1984 | Schmitz et al. | 549/332 |

FOREIGN PATENT DOCUMENTS

| | | | |
|---|---|---|---|
| 3005024 | 8/1981 | Fed. Rep. of Germany | 556/419 |
| 60-006862 | 1/1985 | Japan | 556/421 |
| 0771106 | 10/1980 | U.S.S.R. | 556/419 |
| 2183238A | 6/1987 | United Kingdom | 556/419 |

OTHER PUBLICATIONS

Concern Rises Over Mycotoxin In Grain; Chemical & Engineering News, Oct. 4, 1982, pp. 28-29.
J. March, "Advanced Organic Chemistry," 3rd ed., John Wiley & Sons, 1985, pp. 310-313.
K. Mosbach and K. Nilsson, Separation News, vol. 12 (#3).
SelectiSpher-10 Activated Tresyl HPLAC Columns, Pierce Chemical Co., p. 7.
K. Nilsson and K. Mosbach, Methods in Enzymology, vol. 104, pp. 56-69, Academic Press, (1984).
K. W. Hunter et al., Appl. & Env. Microbiol., 49, pp. 168-172, (1985).
Fun Sun Chu, J. Food Protection, 47, pp. 562-569 (1984).
J. W. Freytag et al., Clin. Chem., 30, pp. 417-420 (1984).
J. W. Freytag et al., Clin. Chem., 30, pp. 1494-1498 (1984).

Primary Examiner—Paul F. Shaver
Attorney, Agent, or Firm—Weingarten, Schurgin, Gagnebin & Hayes

[57] ABSTRACT

A repetitive immunoassay analytical method for determination of a free analyte is carried out by loading an affinity column of covalently bound analyte with tagged antibody, passing a continuous aqueous stream of carrier liquid over the column, introducing an aliquot of a sample to be analyzed for free analyte into the carrier stream upstream of the column, and monitoring the eluting carrier stream for a signal spike resulting from the presence of tagged antibody material released from the column by the application of free analyte in the analytical sample. Many samples may be analyzed by this method before the antibody-loaded affinity column needs to be regenerated. It is also disclosed that substrate-analyte conjugates of superior stability are produced by linking a substrate to a hydroxyalkyl analyte via an amino, hydrazide, or sulfide linking group replacing a hydroxy group. Such stable substrate-analyte conjugates are useful in the production and purification of antibodies, as well as in the repetitive immunoassay of the invention.

3 Claims, 11 Drawing Sheets

REPETITIVE HIT-AND-RUN IMMUNOASSAY AND STABLE SUPPORT-ANALYTE CONJUGATES; APPLIED TO T-2 TOXIN

GOVERNMENT SUPPORT

The government has certain rights in this invention pursuant to contract N00014-84-C-0254, awarded by CRDC and administered by the Office of Naval Research.

FIELD OF THE INVENTION

This invention relates to an immunoassay analytical procedure for determination of an analyte, and to substrate-analyte conjugates, and more particularly to a repetitive hit-and-run immunometric assay and to substrate-analyte conjugates having particularly stable chemical links between the substrate and analyte portions of the conjugates.

BACKGROUND OF THE INVENTION

Introduction

The trichothecenes are a group of fungal by-products with a tetracyclic, sesquiterpenoid ring system. This group includes a number of highly toxic compounds, one of which is T-2 toxin, a mycotoxin produced by fungi of the Fusarium species and isolated from mold found on wheat, barley, oats, and corn (References 1-5). T-2 acts at the cellular level by inhibition of the initiation of protein synthesis (Reference 2). It exhibits some organ specificity, attacking mainly the hematopoietic organs, especially the bone marrow, resulting in marked leukopenia and cellular destruction (Reference 4). Adverse biological reactions are seen in both plants and animals. Phytotoxic effects include stem and leaf scorching and stunting as well as wilting. Similarly, topical application of T-2 toxin to animal or human skin causes local irritation, inflammation, necrosis and desquamation of the epidermis (References 1, 2, and 5). Systemic administration of the toxin to laboratory mice causes a series of fluctuations in respiration and heart rate followed by a slow decline of both until death (References 1 and 5). Epidemiological studies have shown that outbreaks of disease in farm animals in Britain and occurrences of "moldy corn toxicosis" in cattle and commercial flocks of chickens were a result of exposure to T-2 toxin (References 2 and 3). Further, human intoxication, as a result of moldy food consumption, has been traced to this source as well (Reference 9). Thus, because of the poisonous nature of T-2 toxin, and the fact that the grains from which it has been isolated are used as both food and feed, the demonstrated potential for exposure of both humans and animals is apparent. Consequently, sensitive and accurate methods for analysis of T-2 toxin in food and feed are essential.

T-2 Assays

T-2 toxin has been measured by a varity of methods, including: (1) bioassay, (2) thin layer chromatography (TLC), (3) gas liquid chromatography (GC) with flame ionization (FID), electron capture (ECD) or mass spectroscopic (MS) detection, (4) high performance liquid chromatography (HPLC), and (5) immunoassay (References 6-15).

Some of the biological test systems for analysis of T-2 toxin are dermal toxicity, inhibition of protein synthesis, and cytotoxicity. A list of some of the tests used and the detection limit of each for T-2 is given in Table 1. The bioassay is highly sensitive, but it lacks specificity. As a result, one must assume that the biological response caused by administration of a sample extract is due to T-2 toxin and not some other source (References 6 and 9).

TABLE 1

| Biological Assays for T-2 Toxin | |
|---|---|
| Biological System | Detection Limit |
| Rabbit, dermal | 0.01 $\mu$g/test |
| Pea seedling | <1 $\mu$g/ml |
| Brine shrimp | 0.1–0.2 $\mu$g/ml |
| Mouse, intrapertioneal administration | 3.0–5.2 $\mu$g/kg |
| Human karyoblast | <1 $\mu$g/ml |
| Rabbit reticulocytes | 0.03 $\mu$g/ml |

Reference 6, pg. 907

TLC has been a frequently used method for the identification and quantitation of trichothecenes (References 6 and 11). One of the major difficulties associated with this method is low sensitivity. The detection limit for T-2 toxin is generally in the range of 0.1–0.2 $\mu$g/spot (Reference 6). By comparison, bioassays for cytotoxicity can detect T-2 toxin at levels of 0.01–10 ng. It has therefore been suggested that TLC be used in conjunction with bioassay to give a more sensitive and specific testing procedure (Reference 11). A shortcoming of that approach, however, is that more time and expense would be involved. An additional disadvantage of TLC is that closely related structural analogues co-migrate and thus cannot be distinguished from one another.

Gas liquid chromatography has been used to quantitate T-2 toxin in plasma as well as in foodstuffs (References 7-9, and 12). Both packed and capillary columns have been used in combination with FID, ECD, or MS detection. Detection limits achieved by ECD are 2 to 5 fold lower than those obtained by FID (Reference 7). Mass spectroscopic detection is able to reach detection limits for T-2 toxin similar to those reached by ECD (Reference 9). One of the most sensitive GC methods that has been described combines ECD with a packed column in obtaining a detection limit of 25 ng/ml (Reference 12). Gas chromatographic analysis of T-2 is very sensitive, and may have the advantage of allowing the simultaneous determination of several substances. However, performance of an assay for T-2 by this means requires tedious sample preparation and the use of expensive, complex instrumentation. As with TLC, structural analogues as well as matrix substances may be hard to separate from the analyte of interest. Finally, only one sample can be analyzed at a time by gas chromatography. Therefore, screening of large numbers of samples is time consuming and expensive.

HPLC has been used for the measurement of T-2 toxin and other trichothecenes. However, detection of T-2 toxin by HPLC poses a problem because T-2 lacks an ultraviolet or fluorescent chromophore. The detection limit for the analysis, when conducted using a differential refractometer detector, is in the microgram range and unsuitable even for grain analysis. Formation of the p-nitrobenzoate derivative of T-2 toxin increases the sensitivity of the assay to 50 ng/kg, but requires more time and expense. Thus, as other assay systems show more promise, HPLC has seen limited use in quantitating T-2 toxin (References 7 and 10).

Recently, immunoassays have been developed for the measurement of T-2 toxin. These methods involve the simultaneous incubation of samples or standards with a specific antibody against T-2 and a constant amount of T-2 labeled with a signal group such as radioisotope or an enzyme. T-2 in the sample and the labeled T-2 compete for binding to the specific antibody. The bound toxin is separated from the unbound (free) toxin by an appropriate technique, after which the amount of signal in the bound fraction is measured. The concentration of T-2 toxin in the sample is determined by reference to a standard curve (References 10 and 13–15).

In immunochemistry, hydroxy compounds sometimes require coupling to a protein to provide immunogenic material, or to an affinity chromatographic surface to provide an affinity column for purification of generated antibodies. Frequently this coupling must be performed under aqueous conditions either because the protein will only tolerate such conditions, or the hydroxy compound is water-soluble. When aqueous constraints are present, succinic anhydride is used to activate the hydroxy compound (ROH), forming a hemisuccinate derivative ($ROCOCH_2CH_2CO_2H$) that now has a carboxyl functional group. The latter group then can be activated under aqueous conditions for coupling onto an amino site. A difficulty with this approach is that carboxylic acid esters are susceptible to aqueous hydrolysis, and the hemisuccinate leash is therefore unstable. This problem has persisted for many years, limiting the efficiency and performance of protein and affinity surfaces made from hemisuccinate compounds.

The antibody against T-2 has been produced previously by injecting rabbits with a protein T-2 conjugate such as BSA-T-2. In the conjugate employed, T-2 was coupled to protein through a hemisuccinate ester link. This link is unsatisfactory, however, because it hydrolyzes in vivo, releasing T-2. Because of its low molecular weight, unconjugated T-2 is not immunogenic and therefore does not stimulate antibody production in animals. Moreover, unconjugated T-2 can cross cell membranes and enter cells, where it can then exert its toxic effect, and in the case of lymphoid cells, inhibit the organism's immunological response (Reference 15). Therefore, the stability of the BSA-T-2 conjugate employed for antibody production is of utmost importance. Recently, Hunter prepared monoclonal antibodies in an effort to produce T-2 antibodies with high titers (Reference 14). In this work, he showed that nonspecific or enzymatic hydrolysis of a hemisuccinate ester or amide linkage in BSA-T-2 conjugate released T-2, which then inhibited the immunological response. Thus, it is not surprising that polyclonal antibodies to T-2 toxin produced in rabbits have suffered from the disadvantage of low titers; or that enormous effort and cost were required to obtain only two positive hybridomas yielding an antibody of T-2. Although the antibodies produced by hybridomas were not of high affinity, further efforts to obtain better antibodies were discouraged until a more stable T-2 BSA conjugate became available.

Purification of antibodies against T-2 can be carried out by ammonium sulfate precipitation and dialysis, affinity chromatography, or both. In the affinity chromatography approach, BSA-T-2 conjugate was attached to CNBr activated chromatographic material. The modified material was packed into a small column, and the isolated immunoglobulin fraction of ascites fluid was passed slowly over the bed. Unbound immunoglobulins were removed by extensive washing, then T-2 antibody was eluted. Unfortunately, because the BSA-T-2 conjugate employing a hemisuccinate link is unstable, these columns rapidly lose their affinity for T-2 antibody and are not cost-effective.

Both polyclonal and monoclonal antibodies have been used for the analysis of T-2 toxin. Because of the nature of these assays, they are highly specific for T-2, showing little or no interference from other trichothecenes. While assays employing monoclonal antibodies have given higher detection limits (50 ng/tube) than those employing polyclonal antibodies (1 ng/tube) the unlimited production (>10 mg/ml in ascites) potential of monoclonal antibodies should make them valuable as analytical reagents for T-2 analysis (References 13 and 15).

In summary, the advantages of immunoassays are: (1) they are sensitive as well as specific, (2) they are adaptable to the performance of large numbers of assays, (3) they are relatively easy to perform, and (4) they don't require the use of expensive or sophisticated instrumentation. On the other hand, their sensitivity is limited by the poor quality of antibody that has thus far been available, and the unavailability of a stable T-2 affinity column for purifying this antibody.

Immunoassay as an analytical method

Immunoassays have been popular for measuring trace quantities of substances (analytes) since Berson and Yalow described the method in 1958. Most immunoassays use labeled analyte and depend upon the ability of unlabeled analyte (An) to inhibit the binding of labeled analyte (*An) to specific antibody (Ab), when a limited amount of the antibody is present (FIG. 1). After incubation, the reaction reaches or approaches equilibrium. At that time free *An is separated from antibody bound *An and the amount of signal present in one or the other is determined. The analyte concentration in the sample is determined by comparison of the decrease in *An binding produced by free An in the sample to that of a standard curve produced by adding known amounts of An to the assay system. In variations of this assay system labeled antibodies have been used instead of labeled antigen. Such assays are called immunometric assays.

Separation of free analyte from bound can be accomplished by a number of procedures. The most common method is the use of nonspecific adsorbents. Free analyte can be adsorbed from solution by a substance such as charcoal. This method is simple, inexpensive, and fast. Nevertheless, it has certain disadvantages. In some cases, bound as well as free labeled analyte may be adsorbed, and in other cases the affinity of the adsorbent for the analyte may be so high that the equilibrium reaction is disturbed.

Another method of separating free analyte from bound is nonspecific precipitation. Salt or organic solvents are added to the equilibrium mixture to precipitate the antibody fraction. Disadvantages of this method include: (1) variation in results caused by improper mixing, (2) inaccuracies in quantitation caused by coprecipitation of analyte, and (3) high binding blanks caused by nonspecific adherence of labeled analyte to precipitates.

A third method for separating free analyte from bound is the double antibody method. This method depends on the ability of a second antibody to bind to soluble analyte-antibody complexes, causing precipitation of the entire complex. This second antibody is produced so that its binding is directed toward antigenic sites on the first antibody outside of the sites that combine with analyte. Very sensitive measurements are possible using this system and it is applicable to a large number of assay systems. Despite this broad applicability some pitfalls of this method exist. They are: (1) the amount of precipitate is very small and is subject to solubilization during washing if the reaction is not maintained at 4° C., (2) the concentration of first antibody must be high enough to give a precipitate when the second antibody is added, and (3) the titer of the first antibody must be higher than about 1:50 or such a large amount of second antibody must be used that it would be prohibitive.

Free and bound analyte have also been separated on the basis of their difference in electrophoretic mobility and molecular size. These methods have seen limited use because they require expensive equipment, major expenditures of time, and some exposure to hazardous conditions.

Finally, immunologically specific adsorbents have been prepared for separations of free analyte from bound. Either analyte or antibody can be immobilized on a solid surface through a covalent or noncovalent bond. This absorbent is added to the assay where it removes either analyte or antibody from solution, thus facilitating the separation of bound and free analyte. It is preferable to covalently bond the reactant to the surface to prevent it from leaking from the surface into solution. Systems such as this have the advantage of being simple and rapid. However, using this system, one may not always be able to obtain reproducible results, establishment of equilibrium may take many hours in some systems, assays may be less sensitive than comparable solution phase assays, and antibody affinity may fall significantly upon binding to a solid surface.

Traditionally, intact antibodies have been used for immunoassays. However, in the past few years, antibody fragments obtained by enzyme digestion (for example, F(ab')$_2$ and Fab) and in some instances sulfhydryl reduction (Fab') have been used. One such system used an Fab'-$\beta$-galactosidase conjugate with an affinity column for the separation of free analyte from bound (Reference 16). Digoxin was the model analyte. The analysis was conducted as follows: samples or standards of digoxin were mixed with an excess of Fab'-$\beta$-galactosidse conjugate and this mixture was incubated, after which it was passed through a column of immobilized digoxin analogue. Following sample elution, the amount of Fab'-$\beta$-galactosidase in the eluent was measured. The amount of signal in the eluent is directly related to the concentration of digoxin since excess monovalent Fab'-$\beta$-galactosidase is retained by the column. In this system it is to be noted that monovalent antibodies are superior to divalent ones, in that assay sensitivity would be limited for divalent antibodies because a divalent antibody having only one binding site filled would be retained by the affinity column (Reference 16). This assay system is fast, sensitive and adaptable to automation (Reference 17). There are, however, some disadvantages to this analysis scheme. First, the dissociation rate for the analyte-antibody complex must be slow relative to the separation step. If it is not, analyte will dissociate from the antibody complex and allow binding of the released antibody to the affinity column resulting in a reduction in signal elution and a loss of sensitivity. Second, there is an inherent background signal that appears to be variable from lot to lot of Fab'-$\beta$-galactosidase (References 16 and 17). This contributes a variable noise to the system, limiting its accuracy, precision and sensitivity. Third, an excess of Fab' conjugate must be used for each assay tube. At very low concentrations of analyte ($1 \times 10^{-11}$ mol/L) a 100 to 1000 fold excess of Fab'-$\beta$-galactosidase must be used to obtain a usable analysis (Reference 16). This would mean the expenditure of large quantities of conjugate. Fourth, the need to effect a thorough affinity separation may place a limit on the degree to which the column can be miniaturized. Finally, the affinity separation column is not reused, making the assay more expensive to perform and limiting its ability to be miniaturized for in-the-field and in-the-office testing.

Affinity Chromatography

Affinity chromatography is a preparative technique for purifying biological molecules, and has seen little or no use for quantitative analysis in analytical biochemistry. It relies on the biospecific recognition of two biomolecules that form a specific complex. One of these, selected as the ligand, is convalently immobilized on a chromatographic surface. When a solution of the other is passed through such an affinity column, the complementary molecule is selectively retained because of the biospecific complex it forms with the immobilized ligand partner. After residual substances from the sample are washed out of the column with buffer, the elution conditions are changed so that the biospecific interaction is disrupted and the target substance of interest is eluted from the column. Most commonly, this is achieved through a general change in the composition of the buffer eluent such as a change in its pH, ionic strength, content of organic solvent, or presence of a denaturant such as urea. Sometimes ligand elution is performed, in which the biospecific substance to be purified is eluted by the addition of the free ligand to the eluent.

The practice of affinity chromatography is a powerful but imperfect technique. Because of nonspecific binding of contaminants to the column, the column may have a short lifetime or may not fully purify the target substance. The lifetime of the column may also be limited by an instability of the attached ligand, either chemical breakdown or leakage. This problem is more severe when delicate biomolecules are immobilized on the column. The use of general elution conditions such as the change in pH may inactivate some of the target substance, as by denaturation. Ligand elution may not be attractive since free ligand may be expensive, or may not effectively elute a high affinity analyte. Also ligand elution requires an additional step to remove it from the eluted target substance.

SUMMARY OF THE INVENTION

This invention relates to a repetitive immunometric assay method for determination of an analyte, the method including the steps of bonding analyte covalently on a solid support to provide immobilized analyte; providing monoclonal antibody material corresponding to this analyte and capable of noncovalent attachment to the bound analyte, the antibody material also possessing a covalently bonded tag capable of providing an analytically-useful signal; treating the immobilized analyte with the tagged monoclonal antibody material, to form an immobilized complex of analyte and tagged antibody material on the solid support; providing a continuous stream of aqueous carrier liquid across the immobilized complex; injecting into this stream of carrier liquid, upstream of the immobilized complex, an aliquot of a solution to be analyzed for the free analyte, which causes a complex of free analyte and tagged antibody to be eluted from the immobilized complex in an amount related to the amount of free analyte present in the aliquot; monitoring the stream of carrier liquid, downstream of the immobilized complex, for analytical signal indicative of the presence and amount of the tag in the carrier stream; determining the amount of free analyte in the aliquot by comparison of the signal produced with signals produced by addition of known amounts of free analyte to the system; and permissibly repeating the analysis using further aliquots of the same or different solutions to be analyzed for the free analyte.

The invention also relates to compositions containing chemically immobilized T-2 toxin or DAS toxin having the generalized formulae:

T-2: [structure with $(CH_3)_2CHCH_2COO$, $CH_2OCOCH_3$, $OCOCH_3$, linker-leash-substrate]

DAS: [structure with $CH_2OCOCH_3$, $OCOCH_3$, linker-leash-substrate]

in which the structural formulae represent T-2 toxin and DAS toxin respectively, each mycotoxin being absent a hydroxy substituent at the point where the linker unit is attached: the linker is $$\overset{H}{-N-},$$

—CONHNH—, or —S—; the substrate is a macromolecule such as a protein, or a solid support of the sort generally used in chromatography; and the leash is a molecular chain connecting the substrate and the linking unit.

The repetitive immunoassay method is broadly useful for the analysis of analytes at high sensitivities, and the compositions are useful in the production and purification of antibodies against T-2 toxin and DAS toxin, and are also useful in the repetitive immunoassay method which is the primary subject of this invention.

DESCRIPTION OF THE DRAWING

The invention will be better understood from a consideration of the detailed description taken in conjunction with the drawing in which.

DETAILED DESCRIPTION

Figure 1:
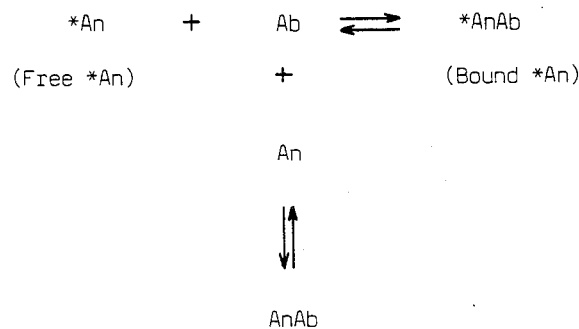
FIG. 1 is a diagram of the principle of radioimmunoassay.
Figure 2:
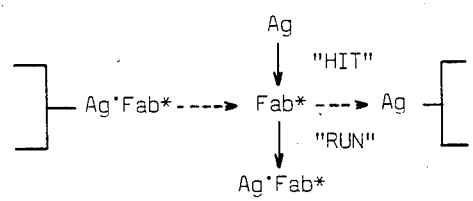
FIG. 2 is an illustration of the concept of hit-and-run immunoassay.

Traditionally, affinity chromatography has been used as a preparative tool. In this invention its analytical capabilities have been exploited in developing a "hit and run" chromatographic technique (FIG. 2). An analytical chromatography column with a ligand covalently immobilized on the surface of a solid support is loaded with labeled monovalent antibody which noncovalently complexes with the ligand. Addition of free ligand (e.g. T-2) elutes a pulse of labeled material from this column, and this is quantitated by the signal provided by the label, e.g., flourescence. This column can thus act as a rapid, repetitive device for detecting ligands such as T-2. Unknown specimens can be done sequentially without the need to reload the column except after many analyses have been done.

Figure 3:
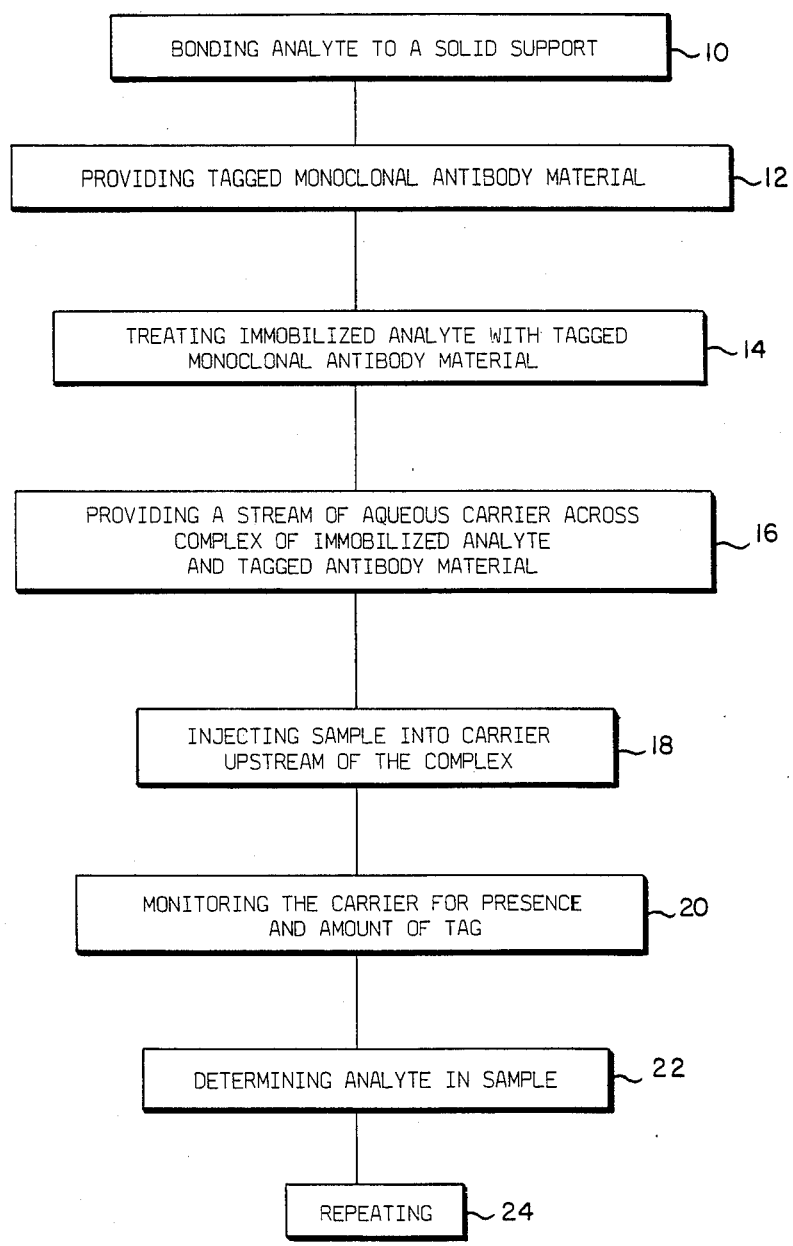
FIG. 3 is an outline of the steps of the hit-and-run immunometric assay method.

Referring now to FIG. 3, there is shown an outline of a repetitive immunoassay method. The first step, 10, is carried out by bonding the analyte to be determined covalently to a solid support to immobilize it. The analyte may be anything which can be bonded to the solid support and which forms antibodies which can be chemically tagged. Examples of analytes to which the method is applicable are toxins such as T-2 and DAS, drugs such as digoxin, drug metabolites such as N-acetylprocainamide, hormones such as insulin, T4, DHT, E2, and infectious disease agents such as viruses. A wide variety of solid supports may be employed, including agarose, cellulose, Sepharose, Trisacryl, polyacrylamide, silica, glass, Immobilon Membrane, and plastic materials such as nylon, polymethacrylate, and polystyrene.

The next step, 12, involves providing monoclonal antibody material corresponding to the analyte and having a chemical tag capable of providing an analytically-useful signal. The monoclonal antibody material may be intact monoclonal antibody, or preferably, a fragment of a monoclonal antibody such as Fab'. Monoclonal antibodies are preferred over polyclonal antibodies because they can be prepared in bulk, they can be more specific for the free analyte being determined, and they are homogeneous. A wide variety of chemical tags are applicable, including enzymes such as RNase, β-galactosidase, glucose oxidase, and horseradish peroxidase, which are monitored by their enzymatic activity; fluorophores such as a phycobiliprotein, rhodamine, fluorescein, and fluorescein plus biotin, which are monitored by their fluorescence; lumiphores such as luminol, isoluminol, and acridinium esters which are monitored by luminescence; radioisotopes, monitored by their radioactivity; dyes, monitored by absorbance; and electrophoric release tags, monitored by gas chromatography. Such release tags and methods of using them are defined in pending U.S. patent application Ser. Nos. 344,394, 591,262, and 710,318, hereby incorporated by reference. Preferred tagged antibody materials are Fab'-fluorescein, Fab'-RNase, and Fab'-lumiphore. In the tagged antibody material, the tag is generally attached to the antibody or antibody fragment via an amino, carboxyl, sulfhydryl, imidazole, or phenolic group on the antibody. The tagged antibody material may contain one or more of these chemical labels. These linkages and their methods of synthesis are known.

The next step, 14, involves treating the immobilized analyte with the tagged monoclonal antibody material to form immobilized complex of analyte and tagged antibody material on the solid support. An excess of tagged antibody material is employed to saturate the immobilized analyte, and subsequently the immobilized complex is washed thoroughly to remove any unbound tagged antibody material or unreacted starting materials.

In the next step, 16, a continuous stream of aqueous carrier liquid is provided across the immobilized complex.

In the following step, 18, an aliquot of the sample to be analyzed for free analyte is injected into the flowing aqueous carrier stream upstream of the immobilized complex. As the carrier stream conveys the sample across the immobilized complex, the free analyte in the solution aliquot complex with tagged antibody material, and elutes from the immobilized complex with the carrier stream. The system operates in this way because while immobilized analyte is held on the solid support, and tagged antibody material is immobile while it is complexed with immobilized analyte on the support, the tagged antibody is in fact not permanently attached to the immobilized analyte, but is in an equilibrium with free tagged antibody material in the aqueous carrier liquid. When free analyte comes in contact with free tagged antibody material, a non-immobilized complex of free analyte and tagged antibody material forms and elutes.

The next step, 20, involves monitoring the stream of carrier liquid, downstream of the immobilized complex, for signal indicative of the presence and amount of the tag portion of the tagged antibody material. The particulars of such monitoring are a function of the tag employed to label the antibody material.

In the next step, 22, the amount of free analyte in the sample aliquot is determined by comparing the signal generated by the released tag with signals generated upon application of known amounts of free analyte to the system.

Finally, as indicated in step 24, analyses may be repeated or new analyses may be performed by injecting succeeding aliquots of the same or different samples, monitoring the signals generated upon applicatin of these successive samples, and determining the amount of free analyte in each sample aliquot, as before. As the system contains a large amount of immobilized complex relative to the amount of free analyte in a given aliquot of sample, many samples may be analyzed before the reservoir of tagged antibody material is depleted to an extent sufficient to detract from the analysis. Upon exhaustion or depletion of the reservoir of immobilized complex, the system is readily regenerated by treating the solid support-immobilized analyte with excess tagged antibody material as in step 14.

An important aspect of this method is that by providing a complex of tagged antibody material on an immobilized analyte, and employing a continuous stream of carrier liquid over this material, the analytical problems caused by damaged antibodies in prior art immunoassay procedures are avoided. In such prior art procedures, a sample containing free analyte is treated with excess tagged antibody and then passed over a column of immobilized analyte to remove the uncomplexed tagged antibody by an affinity-type separation and allow free complex of analyte.tagged antibody to elute from the column, the free analyte being determined by determining the amount of chemical tag in the eluate.

While this prior art procedure is sound in theory, in practice it suffers from the fact that the tagged antibody always has some "damaged" antibody present in addition to the desired tagged antibody in which the antibody is normal. This damaged tagged antibody can be of two kinds: a first kind which does not bind to the immobilized analyte in the affinity column and therefore immediately elutes from the column, and a second kind which absorbs nonspecifically to the affinity column. The net result is that other factors besides the amount of free analyte determine the amount of signal tag eluting from the column, thereby causing the determination of free analyte in an applied sample to be less sensitive, accurate and precise.

In the present procedure these problems are avoided by treating the immobilized analyte with excess tagged antibody material to form a complex of immobilized analyte and tagged antibody on the solid support, and washing this complex by means of the stream of aqueous carrier liquid. In this system, any damaged antibody either washes off the immobilized analyte or binds essentially irreversibly, in either case causing no analytical problems. Although a small amount of tagged antibody material washes out of the system continually, this constitutes a low-level constant background signal which is not an analytical problem. In fact, it can provide a steady-state background signal to help maintain the calibration and status of the system. Thus, when an analytical sample is injected into the flowing stream of aqueous carrier liquid, the signal spike which elutes from the system quantitates the free analyte injected onto the immobilized analyte-tagged antibody complex.

In an alternative embodiment, the free analyte may also move by diffusion or electrophoretic migration across the immobilized complex, causing the movement of the analytical signal, which determines the amount of free analyte. In this case the analysis is also permissably repeated.

The "hit-and-run" immunoassay procedure described above requires analyte covalently bound to solid support, as well as antibodies corresponding to this analyte. The production of such antibodies in turn requires a suitable immunogen and means for purifying the immunoglobulins isolated from a host animal in which the antibodies were produced. When the analyte is a relatively small molecule, it is frequently not immunogenic by itself, and therefore formation of a suitable immunogen requires attachment of the analyte to a carrier molecule, most generally a macromolecule such as a protein. Various techniques for accomplishing this are known. Purification of the antibody produced by action of the protein-analyte conjugate in the host animal is generally carried out by affinity chromatography on a column of analyte covalently immobilized on a suitable solid support. The solid support on which the analyte is covalently bound for purposes of affinity chromatographic purification of antibody may be the same or different from that employed in the hit-and-run immunoassay procedure. As indicated above, various techniques for immobilizing analytes on supports are known. An improved link for joining an analyte to a support is described below, but it not required for the above-described hit-and-run immunoassay method, though it may be advantageously employed in that method.

Whether analyte is bonded to a solid support fo use in the hit-and-run immunoassay or for affinity chromatographic purification of immunoglobulins, or to a macromolecule such as a protein for use as an immunogenic agent (immunogen), it is desirable for the chemical linkage between the substrate and the analyte to be stable, so the substrate-analyte conjugate does not degrade readily. It is an aspect of this invention that an amino, hydrazide, or sulfide functionality employed as the link between a substrate and an immobilized analyte and replacing a hydroxy group on a hydroxyalkyl analyte possesses the requisite stability.

Thus, compounds useful but not required in the practice of this invention are conjugates of the form substrate-leash-linker-analyte where the analyte portion of the conjugate is derived from a hydroxyalkyl analyte by replacement of the hydroxy group of the hydroxyalkyl portion of the analyte with the linker portion of the conjugate. In these hydroxyalkyl analyte-derived compounds, the following definitions apply:

a. The substrate is a solid support or macromolecule, in particular, agarose, cellulose, Sepharose, Trisacryl, polyacrylamide, silica, glass, Immobilon Membrane, a polymeric material such as nylon, polymethacrylate, polystyrene, or a protein such as BSA.

b. The leash is a molecular chain attached to the substrate and to the linker, and is either part of the substrate originally or is attached to the substrate by an appropriate chemical reaction. In the event the substrate is a protein, the leash can be the C-terminal end, the N-terminal end, or a side chain containing an appropriate terminal functional group such as an amine. Where the substrate is a solid support the leash can be derived from a difunctional molecule of from 2 to 10 carbon atoms with the functional groups being such reactive functionalities as carboxylic acids, carboxylic acid halides, carbohydrazides, carboxylic acid active esters, anhydrides, aldehydes, amines, epoxides, hydrazines, thiols, maleimides, alkyl halides, acyl azides, etc. Examples of some suitable leash precursers are adipic acid, diaminooctane, adipic acid dihydrazide, mercaptoethylamine, succinic anhydride, ethylene diamine, hexanediamine, and glutaraldehyde.

c. The linker is $$-N{\overset{H}{-}},$$

—CONHNH—, or —S— which replaces a hydroxy group on the hydroxyalkyl analyte.

d. The analyte may be any hydroxyalkyl material which can be covalently connected to the linker, particular examples being T-2 toxin and DAS toxin. Other exemplary analytes are $E_2$ and DHT.

These hydroxyalkylanalyte-derived materials are preferably formed by reactions between a nucleophile such as an amine, hydrazide, or sulfhydryl group on the leash to the substrate, and a derivative of the analyte bearing a good leaving group such as a sulfonate, resulting in displacement of the leaving group and formation of a stable covalent bond between the substrate and the analyte. This is shown in the following equation:

$$\text{Substrate-leash-nucleophile} + \text{analyte-OSO}_2\text{R}$$
$$\downarrow$$
$$\text{Substrate-leash-link-analyte} + \text{HOSO}_2\text{R}$$

where the substrate and leash are as defined above, the nucleophile is $-NH_2$, $-CONHNH_2$, or $-SH$; and the analyte bears a leaving group such as a sulfonate, on an alkyl portion of the molecule.

The sulfonate ester employed as the leaving group may be any of those known to the art, including tosylate, brosylate, nosylate, mesylate, triflate, nonaflate, and tresylate. The tresyl esters are particularly advantageous analyte derivatives. Other leaving groups known to the art will also serve.

The tresyl esters of T-2 toxin and the closely related toxin DAS, having the structures and respectively, are the preferred intermediates in the preparation of T-2 and DAS-containing conjugates.

Tresyl Coupling

Tresyl chloride (2,2,2-trifluoroethanesulfonyl chloride) is available as an activating agent for coupling amino and sulfhydryl compounds to hydroxymethyl chromatographic supports, as has been reviewed (K. Nilsson and K. Mosbach, Meth. Enz, 104, (1984) p. 56–69). A tresyl sulfonate ester is formed on the chromatographic solid support, giving an activated support (support—$CH_2OSO_2CH_2CF_3$), and this in turn reacts with the amino or sulfhydryl compound ($RNH_2$ or RSH) to achieve covalent immobilization of the latter, giving support—$CH_2$—NHR or support—$CH_2$—S—R.

The advantages of this reaction are that the activated support is stable when stored at low pH; the activated support will react efficiently with an $RNH_2$ or RSH under aqueous conditions at pH 7.5; and the final linkages obtained are stable. Other activating agents for hydroxymethyl surfaces have not combined these desirable properties as successfully. Both Pharmacia and Pierce have made tresyl-activated affinity supports available commercially. Polyethylene glycol, a hydroxy compound, also has been tresyl-activated for coupling to a protein (K. Nilsson and K. Mosbach, Ibid.).

In other reported work, Mosbach, et al (Mosbach, K. H.; Furulund; Nilsson, K. G. I., Method of Covalently Binding Biologically Active Organic Substances to Polymeric Substances, U.S. Pat. No. 4,415,665, Nov. 15, 1983) have described the activation of a hydroxy-containing polymeric carrier by tresyl chloride or an analogous sulfonyl halogenide. This activated surface can then be reacted with a biologically active organic substance containing a primary or secondary amino group, thiol, or aromatic hydroxy group. However, hydrazide coupling to a hydroxyalkyl group activated with a sulfonyl halogenide has not been described.

Tresyl-hydrazide coupling

In the present invention the problem of stable coupling of T-2 to a protein or affinity surface is overcome by using tresyl chloride-activated T-2 and specified nucleophilic groups on the substrate. As stated above, ordinarily tresyl chloride is used to activate an affinity surface for coupling to an amino or sulfhydryl compound. This invention has significantly broadened its use by activating instead the T-2 hydroxy compound for coupling to a surface, thus bridging the distant worlds of activating an affinity surface and preparing a novel derivative of T-2 for aqueous coupling. Also, the introduction of a new coupling technique for a tresyl-activated compound, reaction onto a hydrazide site, has the advantage that the resulting alkyl-hydrazide linkage is noncharged at neutral pH, whereas an alkyl-amino linking gives a positive charge. The latter charge is generally undesirable because it not only imposes an ion exchange site on the affinity material, complicating the chromatographic characteristics of the affinity material, but this charge significantly changes the chemical nature of the hydroxy compound. This may interfere, for example, with the recognition of the latter compound in the attached (surface-immobilized) forms of this compound. It is important for both purification of a T-2 antibody (an antibody that specifically recognizes T-2), and for the use of such an antibody in an immunoassay for T-2, that surface-attached and free forms of T-2 are both recognized by the antibody.

Other conjugates useful in the practice of the invention are tagged fragments of monoclonal antibodies, Fab'-tag, where the antibody fragment Fab' is derived from pepsin catalyzed cleavage of an antibody, and the tag is as previously defined. Particular Fab'-tag conjugates of interest are those in which the Fab' is a fragment of T-2 antibody and the tag is one or more molecules of fluorescein, RNase, β-galactosidase, glucose oxidase, horseradish peroxidase, luminol, isoluminol, an acridinium ester, a release tag, or a dye. Also of interest is the conjugate Fab'-tag in which the Fab' fragment is derived from DAS antibody and the tag is one or more of those listed above.

The substrate-leash-linker-analyte conjugates of the invention employing as the linker an amino, hydrazide, or sulfide linkage are not restricted to use in the hit-and-run immunoassay procedure, but are broadly useful in analytical biochemistry wherever stable conjugates of an analyte chemically bonded to a substrate are needed. In particular, the conjugates in which the substrate is a macromolecule such as a protein are generally useful as immunogenic agents (immunogens) to induce formation of antibodies in an animal against the covalently bound analyte. Although substrate-analyte conjugates are known for this purpose and the procedures for antibody production and isolation are also known, the improved conjugates produced by employing as the linking unit an amino, hydrazide, or sulfide group in place of a hydroxy group on a hydroxyalkyl analyte are worthwhile.

Similarly, the substrate-leash-linker-analyte conjugates of the invention are also more broadly useful in the area of affinity chromatography for the purification of antibodies. Although affinity chromatography for this purpose is known, the linkages employed in the present conjugates are more stable than those of the prior art and therefore produce more stable and long lasting affinity chromatography supports for hydroxyalkyl substances.

Employment of an $$\overset{H}{-N-},$$

—CONHNH—, or —S— linkage to join a substrate and a hydroxyalkyl analyte is advantageous because such links are stable relative to those of the prior art. Thus, protein-analyte conjugates so linked employed in antibody production do not hydrolize readily in vivo, so produce antibodies efficiently. Similarly, chromatographic columns packed with covalently bound antibody so immobilized do not lose bound analyte readily, and so retain their affinity properties.

EXPERIMENTAL SECTION

Materials

Bovine pancreatic ribonuclease A (Type IIIA) (RNase), polycytidylic acid (Poly C), cytidine 2'-3' cyclic monophosphate, bovine serum albumin (BSA), N-ethylmaleimide, 2-mercaptoethylamine, 5,5'-dithiobis (2-nitrobenzoic acid) (DTNB), trinitrobenzene sulfonic acid (TNBS), and iodoacetamide were obtained from Sigma Chemical Co. (St. Louis, Mo.). Citraconic anhydride and mercaptoethanol were from Eastman Organic Chemical (Rochester, NY). Dimethylformamide (DMF), dimethyl sulfoxide (DMSO), and immobilized pepsin were purchased from Pierce Chemical Co. (Rockford, Ill.). Fluorescein isothiocyanate was obtained from Aldrich Chemical Co. (Milwaukee, Wis.). N-γ-maleimidobutyryloxysuccinimide (GMBS) and Biotin-X-NHS were from Calbiochem-Behring (Layolla, Ca.). Lanthanum acetate was purchased from Alfa Products (Danvers, Ma.). Ascites fluid containing anti T-2 monoclonal antibody was provided by Ken Hunter and was prepared by the procedure published in his paper (Reference 14). 3-[3H]T-2 toxin was from Amersham (Arlington Hts., Ill). T-2 Toxin was obtained from the Myco-Lab Company (Chesterfield, Mo.). Buffer salts were purchased in the highest purity available from Fisher Scientific (Medford, Ma.). Agarose adipic acid hydrazide was obtained from P-L Biochemicals (Milwaukee, Wis.). 2,2,2-Trifluoroethanesulfonyl chloride was purchased from Aldrich Chemical Company (Milwaukee, Wis.).

Preparation of Fab',Fab'-fluorescein, and Fab'-RNase, and Size exclusion FPLC chromatography Fab' was prepared by digesting antibody (obtained and purified as defined below) with pepsin followed by reduction with mercaptoethylamine. This product was reacted directly with maleimido-citraconyl-RNase (see below), which is de-citraconylated during the conjugation to Fab' to give Fab'-RNase. For the preparation of Fab'-fluorescein, the reduced Fab' was capped with iodoacetamide and then reacted with fluorescein isothiocyanate.

The purity and molecular weight of the antibody fragments and derivatives were determined on a Superose 12/30 column (Pharmacia) using a Pharmacia FPLC. The elution was carried out in 0.1M $NaH_2PO_4$, 6M guanidine HCl pH 7.5 at 0.3 ml/min, 0.2 AUFS. The amount of protein injected was between 50 and 100 μg. Unless otherwise stated, the concentrations of antibody and its fragments, F(ab')$_2$ and Fab', were calculated from the absorbance at 280 nm by using an extinction coefficient of 1.5 cm$^2$/mg for the antibody and 1.48 cm$^2$/mg for F(ab')$_2$ and Fab'.

Size exclusion FPLC was used to monitor the enzyme cleavage, chemical reduction, and conjugation reactions of T-2 monoclonal antibody. The monoclonal antibody eluted as a single peak with a molecular weight of 158,000. After incubation of the antibody with immobilized pepsin for 20 hr, a shift in the peak maximum was observed to M.W. 103,000, corresponding to F(ab')$_2$. Treatment of F(ab')$_2$ with mercaptoethylamine followed by acetylation with iodoacetamide resulted in the disappearance of the peak at MW 103,000 and appearance of a new peak at MW 57,000 (Fab'). Finally, both Fab-RNase and Fab'-fluorescein were similarly characterized and found to have MW of 56,000 and 54,000 respectively.

Preparation of Fab'-fluorescein conjugate

Anti T-2 monoclonal antibody was purified from mouse ascites fluid by protein A affinity chromatography using the Bio Rad MAPS procedure (Reference 21). After purification, the antibody was dialyzed overnight vs 4 l of 0.02M sodium acetate pH 7.0. The pH of the solution was lowered to 4.2 with glacial acetic acid and 0.25 ml of immobilized pepsin were added for each 10 mg of antibody to be digested. Digestion was stopped after 20 hr by removing the pepsin beads and raising the pH of the solution to 7.0 with 1N NaOH. The digest was reapplied to the protein A column to remove residual undigested antibody and pFc fragments. The unretained fraction from the protein A chromatography, containing the F(ab')$_2$ fragment, was dialyzed overnight vs 4 l of 0.1M $NaH_2PO_4$, 5 mM EDTA pH 6.5 and concentrated from 40 to 20 ml of repetitive use of a Centricon 30 Microconcentrator (Amicon). Reduction of the F(ab')$_2$ fragments was accomplished by addition of 0.1 ml of 0.1M mercaptoethylamine for each milligram of F(ab')$_2$ and incubation at 37° C. for 90 minutes. The sulfhydryl groups on the resulting Fab' fragments were alkylated by adding 0.1 ml of 0.2M iodoacetamide per milligram of protein and mixing for 60 min at room temperature. The mixture was desalted on a Sephadex G-25 column (1.6×40 cm) equilibrated with 50 mM $NaH_2PO_4$ 150 mM NaCl pH 7.2. The alkylated Fab' fragments which eluted in the void volume were pooled, the pH was adjusted to 9.5 with 1N sodium hydroxide, and 6 mg of fluorescein per milligram of Fab' were added. After mixing for 2 hr at room temperature, the labeled protein was purified on a Sephadex G-25 column (1.6×40 cm). The fractions containing the labeled protein were pooled and concentrated to a volume of 15 ml in a Centricon-30 Microconcentrator (Amicon).

Degree of fluorescein labeling of Fab'

The number of fluorescein molecules coupled to Fab', giving Fab'-fluorescein, was calculated from the absorbances at 280 nm and 495 nm as described by The and Feltkamp (Reference 22). Calculations were performed according to the following formula: flourescein/protein=(2.87 $A_{495}/A_{280}$−0.35 $A_{495}$). From this it was determined that the fluorescein conjugate Fab'-fluorescein contained 4.7 moles of fluorescein per mole of Fab'.

Preparation of Maleimido-citraconyl-RNase

In order to protect amino groups critical for enzymatic activity, ribonuclease was treated with a 30 fold molar excess of citraconic anhydride over the number of amino groups. One hundred twenty milligrams (8.8 μmol) of RNase were dissolved in 6 ml of 0.12M HEPES pH 7.5 and 23.7 μl (264 μmol) of citraconic anhydride were added. This solution was mixed for 10 min at room temperature while the pH was maintained at 7.0 with 1N NaOH. This reaction blocks approximately 9 of the amino groups of the native RNase. Subsequently, 100 μl of DMF containing 60 mg (215 μmol) of GMBS were added and mixing was continued for 30 min to block most of the remaining amino groups with GMBS. Then, the reaction mixture was desalted using a PD-10 column with 0.005M sodium acetate pH 6.0 as the eluent. The void volume fractions containing the protein were pooled and lyophilized.

Number of amino groups modified by GMBS in maleimido-citraconyl-RNase

Twenty-five μl (0.35 μmol) of mercaptoethanol in 0.1M $KH_2PO_4$ pH 7.0 were added to 1.0 ml (0.22 μmol) of citraconylated GMBS RNase (1.6 maleimide residues/RNase) in the same buffer. The reaction mixture was stirred for 10 min at room temperature and subjected to gel filtration on a PD-10 column with 0.12M HEPES pH 7.5 as eluent. Deblocking of amino groups modified by citraconic anhydride was accomplished by adjusting the pH of the product from the PD-10 column to 2.5 with 0.1M HCl and mixing at 37° C. for 2 hr. The number of modified amino groups, relative to native RNase, was determined by means of the TNBS test (Reference 18) before and after deblocking. Briefly, 100 μl of protein solution (0.5 mg/ml) were added to 900 μl of 0.1M $NaBO_4$ pH 9.3 followed by 100 μl of 0.03M TNBS in water. Samples were incubated for 30 min at room temperature and the absorbance was measured at 340 nm. It was thus determined that about 10 of the amino groups were blocked by the combination of citraconic and GMBS blocking groups. After HCl deblocking to remove anhydride blocking groups, 1.4 amino groups were found to be still modified by GMBS. This result corresponds well with the number of maleimide groups that were measured by the Ellmans reaction, reported below (Reference 19).

Determination of maleimide groups in citraconylated GMBS RNase

The number of maleimide groups incorporated per mole of RNase was determined by a modification of the method of Ellman, et al, (Reference 19). Mercaptoethanol standards (5–100 nmol) and RNase samples (10–70 nmol) were prepared in 1 ml of 0.1M KH$_2$PO$_4$20 mM EDTA pH 7.2. One hundred nanomoles (1 ml) of a freshly prepared solution of the mercaptoethanol in the same buffer was added to all tubes. After incubation at 37° C. for 1 hour, 3 ml of 0.4M TRIS HCl, 20 mM EDTA pH 8.9 and 0.1 ml of 10 mM DTNB (in methanol) were added. The tubes were incubated for 10 minutes at room temperature, after which the absorbance at 412 nm was measured. Approximately 1.2 maleimide groups per RNase molecule were found.

Preparation of FAB'-RNase conjugate

Figure 12:
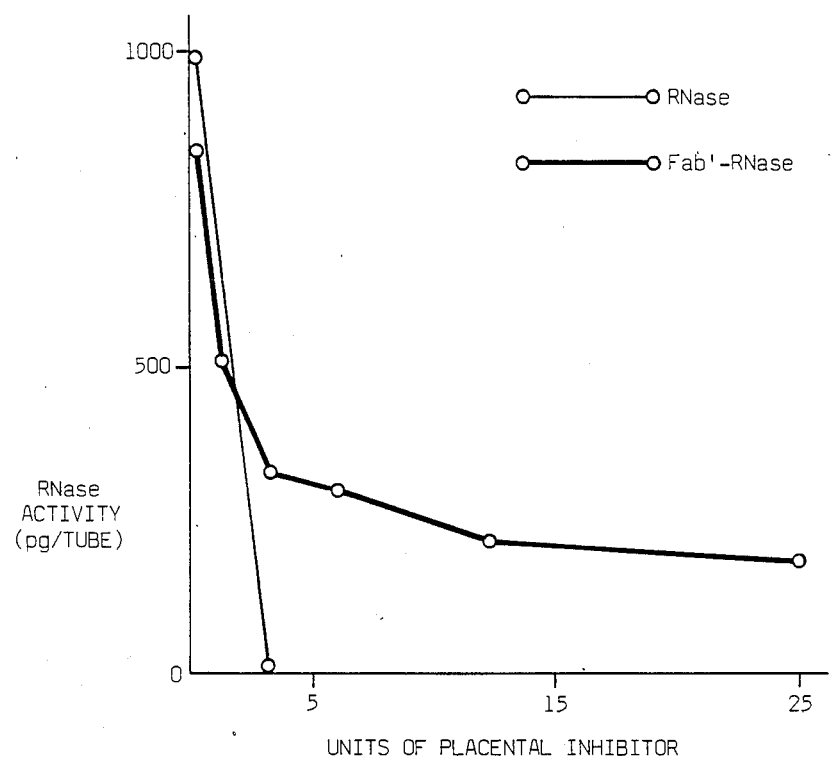
FIG. 12 shows resistance of the enzymatic activity of Fab'-RNase to placental inhibitor.

Anti T-2 monoclonal antibody was digested and reduced as described above for preparation of the fluorescein conjugate, with the exception that the sulfhydryl groups of the Fab' fragment were not alkylated with iodoacetamide. Fab'(7.4 mg) in 25 ml of 0.1M NaH$_2$PO$_4$ 5 mM EDTA pH 6.5 was mixed with citraconylated GMBS RNase (45.64 mg). This mixture was stirred overnight at 4° C., concentrated to a volume of 10 ml by ultrafiltration on a Centricon-30 Microconcentrator, and purified by gel filtration on a column (1.6×40 cm) of Sephadex G-75 with 50 mM TRIS HCl 150 mM NaCl pH 7.2 as the elution buffer. The fractions containing the Fab'-RNase conjugate were pooled and the volume was reduced to 10 ml using Centricon-30 membrane filters. Fab'-RNase was found to be resistant to inhibition by placental inhibitor, as shown in FIG. 12.

Determination of RNase activity in maleimido-citraconyl RNase and Fab'-RNase conjugate Monomeric substrate: One milligram of cytidine 2',3' cyclic phosphate was dissolved in 10 ml of 0.5M TRIS HCl, 5 mM EDTA pH 7.5. Eight hundred microliters of this solution were pipetted into 1 ml cuvettes, 100 μl samples of RNase (10–100 μg) were added, and the change in absorbance at 284 nm with time was measured.

Polymeric substrate: RNase standard (30–1000 pg) and sample solutions were prepared in 0.5M TRIS HCl, 5 mM EDTA, 0.1% BSA pH 7.5. Fifty microliters of each solution was added to 100 μl of 0.5% poly C(w/v in water). The tubes were incubated at 37° C. for 30 min, placed in an ice bath, and 50 μl of ice cold 14 mM lanthanum acetate in 24% perchloric acid were added. After a 15 min incubation the tubes were centrifuged at 1700×g for 20 min at 4° C. A 100 μl aliquot was withdrawn from the supernatant, diluted 10 fold with water and the absorbance measured at 260 nm.

This will be useful for distinguishing the enzymatic activity of Fab'-RNase from background RNase activity that may be encountered in a sample undergoing chemical analysis.

The enzymatic activity of maleimido-citraconyl RNase towards 2'3' cytidine cyclic phosphate after deblocking increased from 51% to 94%. Moreover, up to 68% of the acitivity towards poly C was recovered. The enzymatic acitivity was measured after reaction of the maleimide RNase derivative with mercaptoethanol to avoid cross-linking during the activity study.

The RNase activity of the Fab'-RNase conjugate toward both monomeric and polymeric substrates was measured. The amount of activity on a molar basis of this conjugate, relative to that of native ribonuclease, is 5% with 2'3' cytidine cyclic monophosphate as a substrate and 2% with polycyticylic acid substrate.

Preparation of 14 C succinylated ribonuclease

Ribonuclease (200 mg; 1.617 μmol) was dissolved in 35 ml of DMSO containing N-methylmorpholine (1634 μmol) and dimethylaminopyridine (1.47 μmol). Succinic anhydride (1.25 mg; 12.55 μmol) was dissolved in 1 ml of dry DMSO and added to 250 μCi (2.15 μmol) of $^{14}$C succinic anhydride. The succinic anhydride solution was vortexed and added to the ribonuclease mixture. The $^{14}$C succinic anhydride vial was washed once with DMSO and this wash was added to the reaction mixture. After shaking overnight at room temperature the reaction mixture was dialyzed for 48 hr vs 5×4 l distilled water. The dialysate was lyophilized and stored at −20° C.

Number of RNase molecules per mole of Fab'

Citraconylated GMBS RNase was prepared according to the procedure previously described, except a mixture of $^{14}$C succinylated and native RNase with a specific activity of 164 cpm/μg was used. $^{14}$C succinylated citraconylated GMBS RNase (2.7 mg) was dissolved in 0.1M NaH$_2$PO$_4$, 5 mM EDTA pH 6.5 containing 5.4 mg Fab'. The reaction was allowed to proceed overnight on a Nutator at 4° C. The conjugate was isolated by gel filtration on a column (1.6×80 cm) of ACA 44 (LKB) with 10 mM TRIS HCl, 150 mM NaCl pH 7.2 as the eluent, and showed a specific activity of 63 cpm/μg. The number of moles of RNase per mole of Fab' was calculated from the concentration of protein per ml of conjugate as determined by the Pierce assay (Reference 23) and the number of counts of $^{14}$C as determined by liquid scintillation. By this method it was determined that 1.1 moles of RNase are coupled to 1 mole of Fab'.

Binding of Fab'-fluorescein and Fab'-RNase to T-2 affinity gel

Two hundred microliters of T-2 affinity gel (see below) were packed into a 1 ml Supelclean (Supelco) polypropylene filtration column having a polyethylene frit. The column (0.5×1 cm) was equilibrated with 10 ml of 0.01M TRIS HCl pH 7.5 after which 2 ml (0.8 A$_{280}$/ml) of either Fab'-fluorescein or Fab'-RNase were applied. The column was washed with 10 ml of equilibration buffer and eluted with 10 ml of 1N NH$_4$OH pH 11.6. Absorbance was monitored at 280 nm and fractions were collected in acetic acid to maintain the pH at 7.0. Samples were taken to measure protein recovery and the rest of the pooled fractions were recycled through the T-2 affinity column.

A portion of each conjugate (23.4% of Fab'-fluorescein, 40% of Fab'-RNase) was not retained by the column, indicating some antibody binding sites for T-2 had been damaged or blocked during the digestion or the chemical modification process. Of the total Fab'-fluorescein applied to the column, 15% was eluted with 1M NH$_4$OH. This left 62% of Fab'-fluorescein unaccounted for. Corresponding work with Fab'-RNase resulted in 39% being eluted by 1M NH₄OH and 21% unaccounted for.

Figure 4:
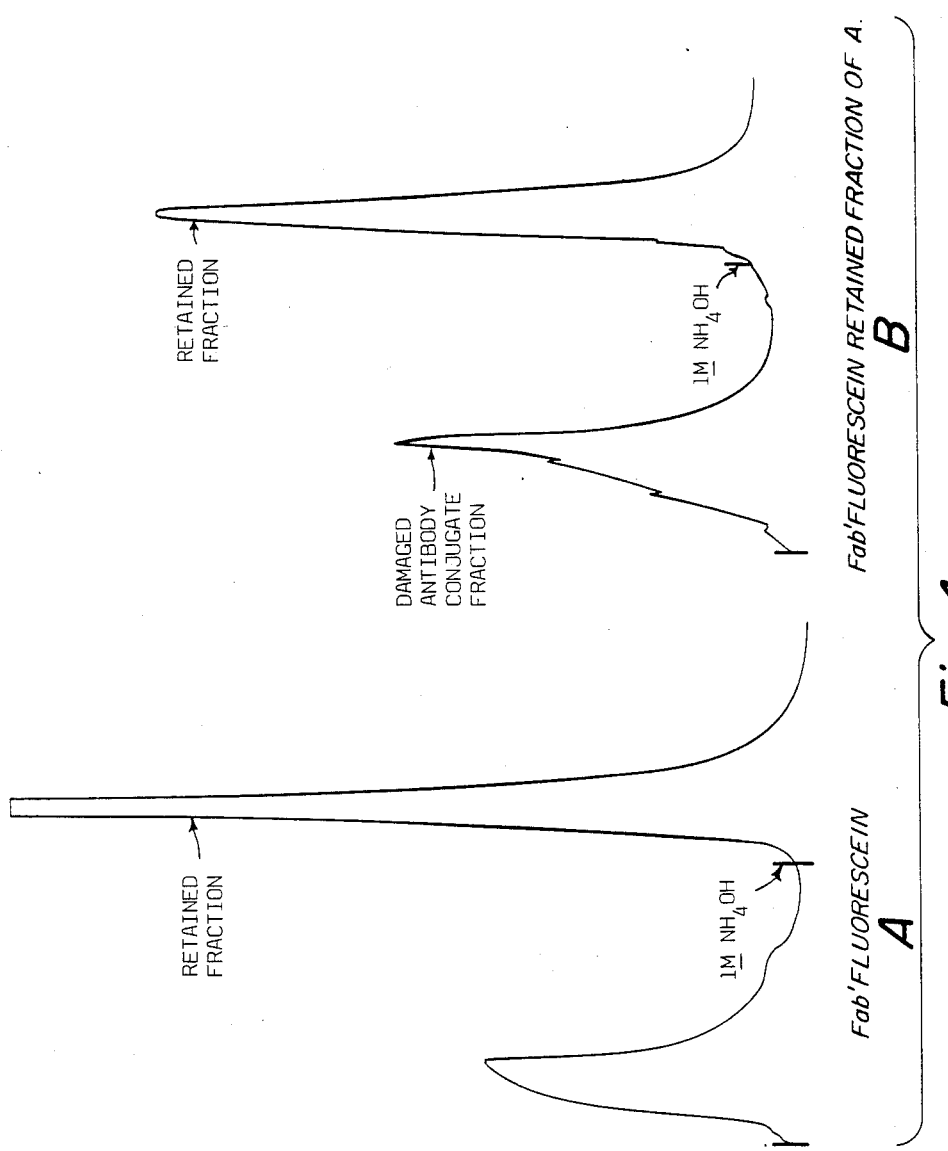
FIG. 4A is an elution pattern of Fab'-fluorescein from a T-2 affinity gel.
FIG. 4B is an elution pattern of retained peak from FIG. 4A when applied to a T-2 affinity gel.
Figure 5:
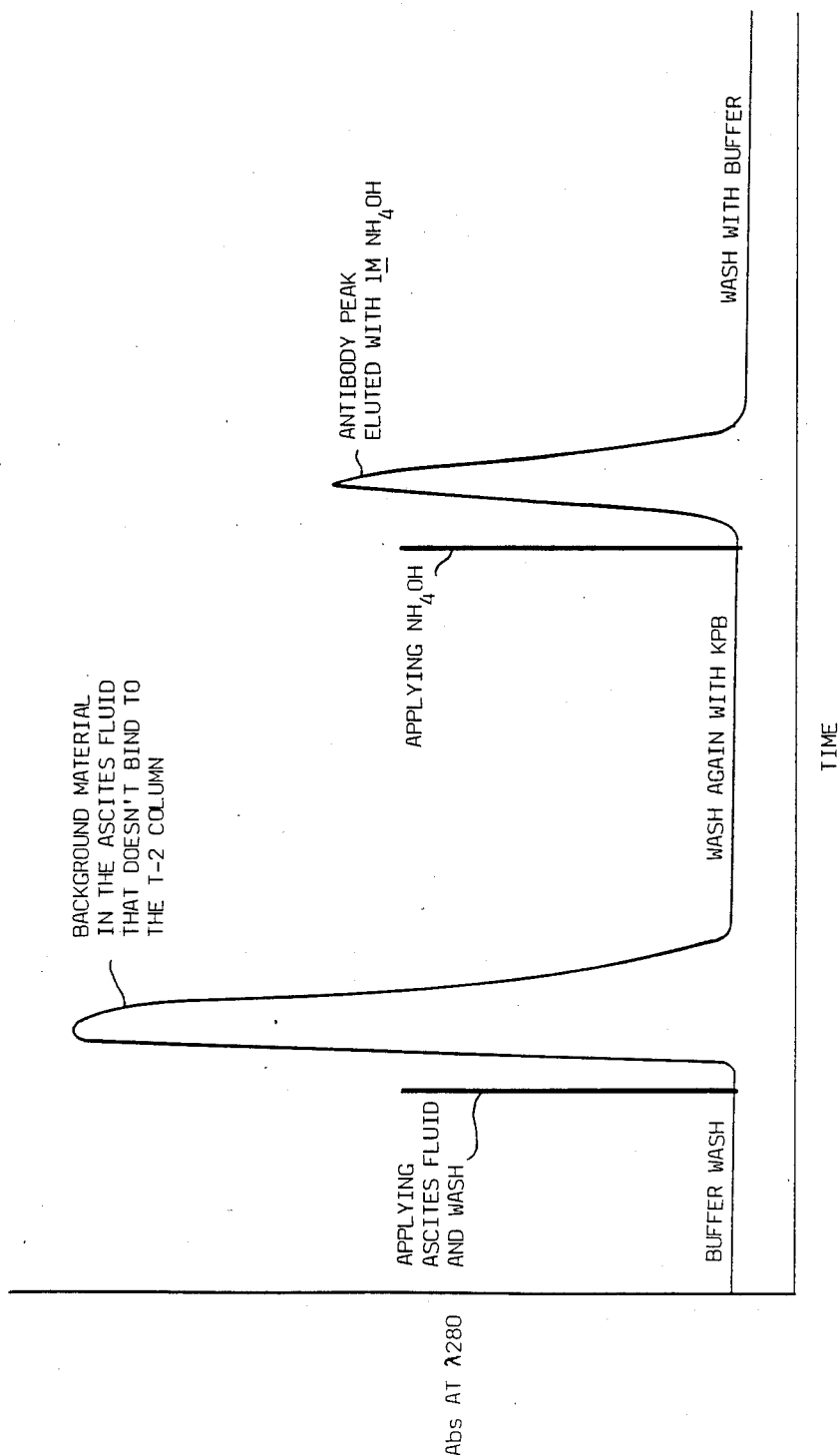
FIG. 5 is an elution chromatogram showing purification of T-2 antibody on a T-2 affinity column.
Figure 6:
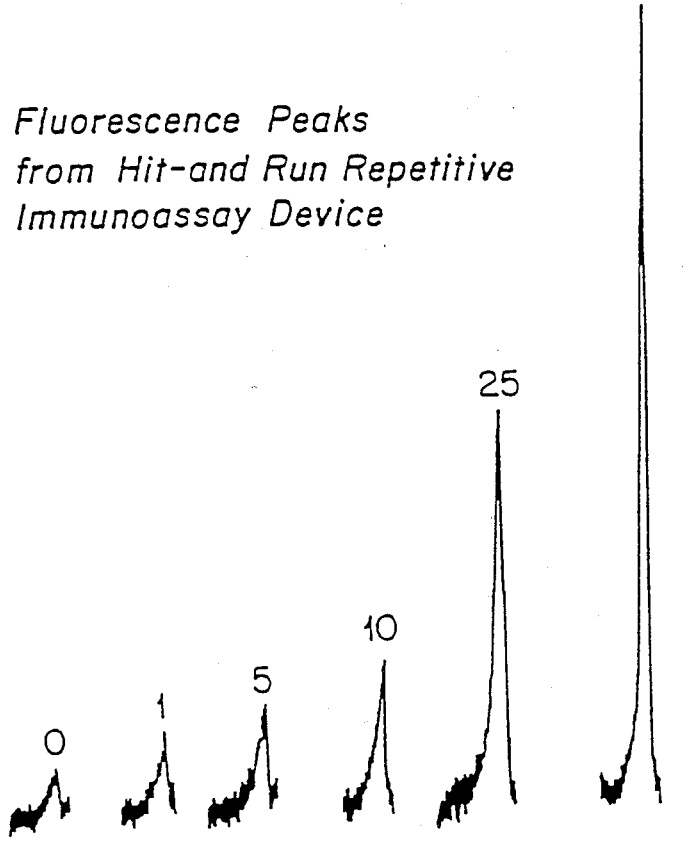
FIG. 6 shows signal pulses of fluorescence resulting from application of 0 to 50 ng of T-2 toxin in the repetitive immunoassay.
Figure 7:
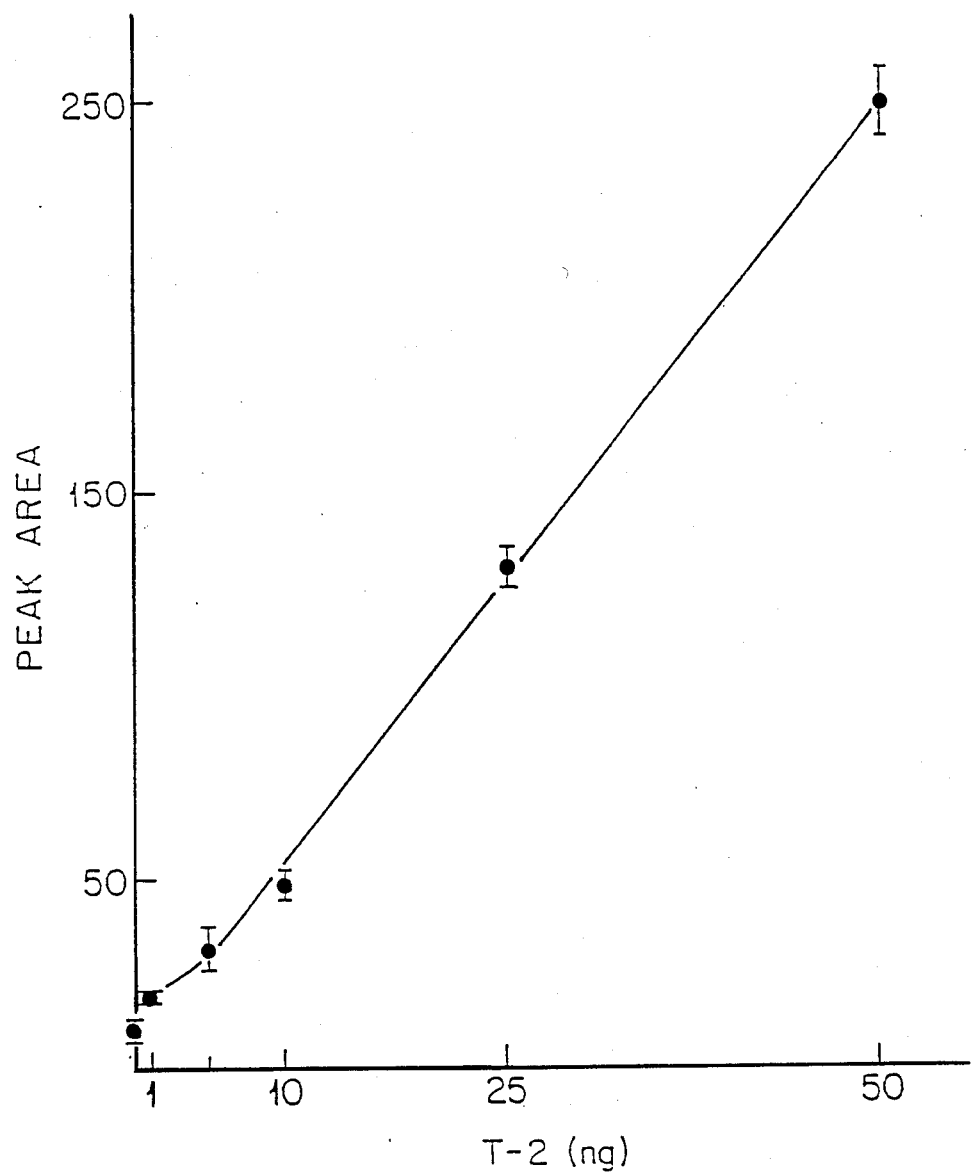
FIG. 7 is a standard curve for detection of T-2 in the repetitive immunoassay using Fab'-fluorescein.
Figure 8:
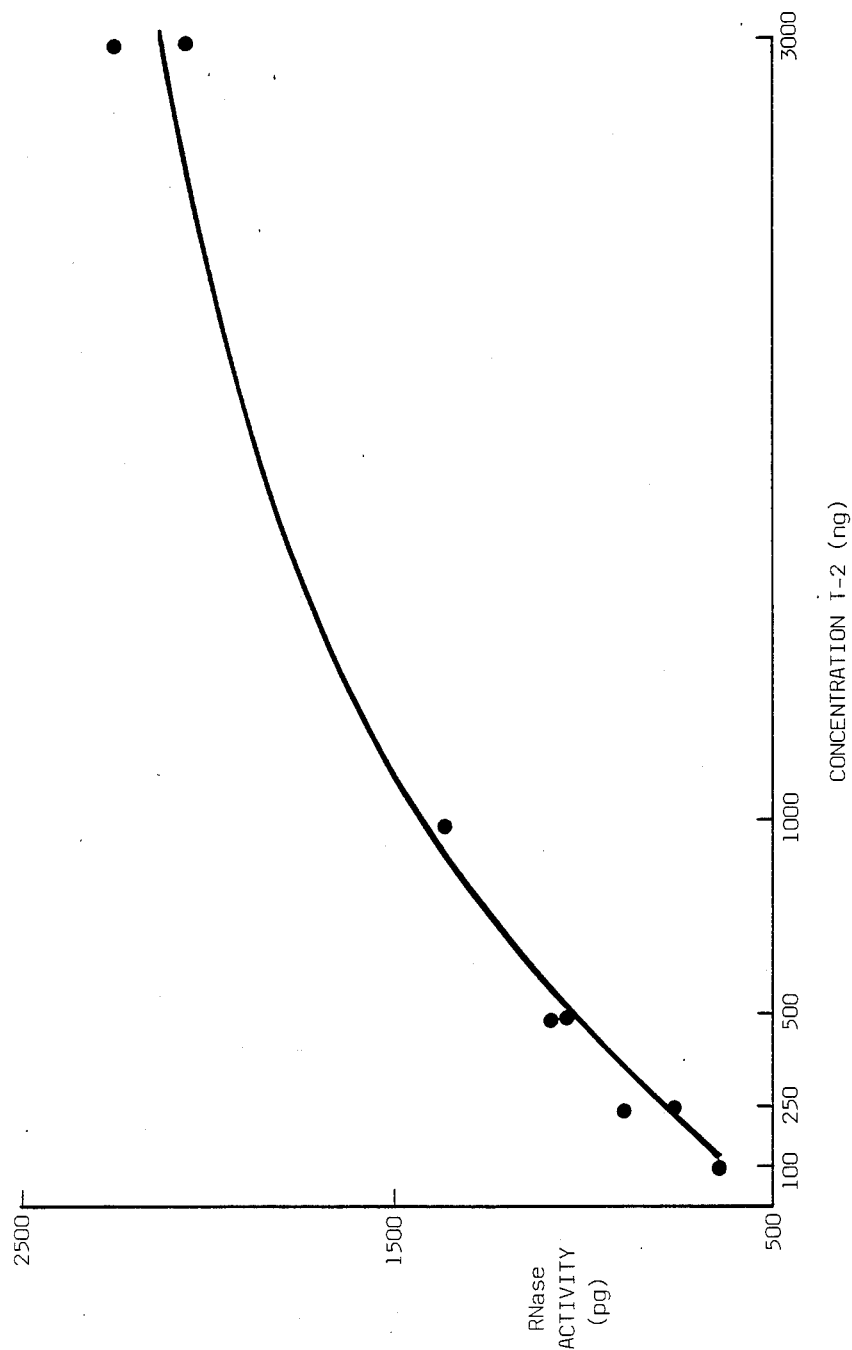
FIG. 8 is a standard curve for detection of T-2 in the repetitive immunoassay using Fab'-RNase.

Subsequently, the eluted fractions of both the Fab'-fluorescein and the Fab'-RNase were reapplied to the column and again eluted with 1M NH₄OH. As before, a portion of each conjugate was not retained. This further indicated that some damage occurs to the T-2 binding site of both conjugates under the elution conditions used. This is shown in FIG. 4 for Fab'-fluorescein. Fab'-RNase gave similar results. Similar results were obtained where the Fab'-fluorescein was eluted from the affinity gel with excess T-2, dialyzed exhaustively to remove T-2, and re-applied to the T-2 affinity column.

Preparation of [$^3$H]T-2/T-2 mixture

Five hundred microliters of [$^3$H]T-2 (11 Ci/mmol) were mixed with 45 mg of T-2 after which the solvent was evaporated and the resulting powder was dried using high vacuum. Subsequently the mixture was recrystallized from benzene/hexane. The yield was 34 mg (76% recovery). The specific activity of the crystallized material was 27 cpm/μg.

Preparation of T-2 Toxin tresyl ester

To a solution of 34 mg (0.072 mmol) 3-[$^3$H]T-2 toxin (25,000 dpm/mmol) in 2 ml of dry actone, 35.5 ml (0.437 mmol) pyridine and 48.5 ml (0.439 mmol) 2,2,2-trifluoroethanesulfonyl chloride were added at 0° C. The reaction mixture was stirred for 3 hr. under nitrogen at room temperature. At this time the reaction was complete as determined by TLC (toluene:ethyl acetate:formic acid, 6:3:1 v/v/v). The solvent was evaporated to dryness and the residue was redissolved in 15 ml of ethyl acetate. The organic layer was washed three times with cold 5 mM HCl, once with cold water, and dried over anhydrous sodium sulfate. The solvent was evaporated and the product was dried under high vacuum, giving a white powdery material that was stored at −15° C.

Preparation of T-2-toxin-adipic acid hydrazide-agarose affinity gel

Agarose-adipic acid hydrazide gel (5 ml, PL Biochemicals) containing 1–6 μmole of hydrazide/ml of gel was washed with 20 ml each of water and a mixture of DMSO/0.01M potassium phosphate buffer pH 7.2 (70/30 (v/v)). The gel was suspended in the same mixture containing 18.4 mg (30 μmol) of [$^3$H]T-2 toxin tresyl ester. After shaking for 3.5 hr at 4° C., the gel was washed on a sintered glass funnel with 20 ml of the above DMSO/buffer, 20 ml of methanol/buffer (70/30 v/v), and finally with 20 ml of buffer. The gel was stored in the DMSO/buffer mixture at 4° C. The amount of T-2 toxin bound to the agarose gel was $\geqq$0.2 μmol/ml of gel based on the content of radioactivity.

the T-2 toxin-agarose was found to bind 6 mg of anti T-2 antibody per ml of gel, which antibody could be fully eluted with T-2. The antibody complexed on the T-2 column did not elute with a variety of chaotropic agents. However, non-specific elution was achieved with 1M ammonium hydroxide, pH 11.6, at 4° C. After dialysis, 70–80% of the total protein applied to the column was recovered as fully active antibody. A typical elution profile is shown in FIG. 5.

Stability of T-2 agarose affinity gel

The stability of T-2 toxin agarose gel to 1M ammonium hydroxide pH 11.6 was investigated according to the following procedure. Excess antibody was applied to the same T-2 affinity gel column (0.5×1.3 cm) in three consecutive runs, each time eluting with 1M ammonium hydroxide. After each run, the eluent was dialyzed and the amount of antibody eluted was measured by both the Lowry protein assay (Reference 20) and absorbance at 280 nm. No decrease in the binding capacity of the T-2 affinity column was observed (0.94±0.08 mg).

Purification of anti T-2 from ascites by T-2 affinity chromatography

The following experiment was performed in a cold room at 4° C. T-2 affinity gel (900 μl) was packed into a 1 ml Supelclean (Supelco) filtration column. The gel bed (0.5×4.6 cm) was washed with 20 volumes of 0.01M potassium phosphate pH 7.2. The ascites fluid (0.5 ml), containing ~5 mg of anti T-2 monoclonal antibody, was applied to the column at a flow rate of 0.6 ml/min. Unbound protein was removed by washing with the same buffer until baseline absorbance was achieved at 280 nm. The T-2 antibody was eluted with 1M $NH_4OH$ pH 11.6. The pH of the fraction was immediately adjusted to 6 with 50% acetic acid, and then dialyzed for 48 hr vs 2×4 l of 0.01M potassium phosphate, 0.05% $NaN_3$ pH 7.2. After the elution, the column was washed again with 0.01M potassium phosphate pH 7.2 and stored at 4° C. The T-2 antibody concentration was determined by measuring the absorbance at 280 nm and calculating with an extinction coefficient of 1.5 cm$^2$/mg. Molecular weight characterization was performed according to the procedure previously described. The integrity of the anti T-2 antibody was determined by the [$^3$H]T-2 toxin binding assay previously described.

Determination of the titer of T-2 antibody

The affinity purified ascities fluid (0.306 mg/ml) was diluted with 0.01M sodium phosphate, 0.9% NaCl, pH 7.2 (1:2, 1:5, 1:10, 1:20, 1:40, 1:80 and 1:160). Dextran coated charcoal was prepared by mixing 5 g of activated Norit-A charcoal and 0.5 g of Dextran (T-70) in 480 ml of 0.01M sodium phosphate, 0.9% NaCl, 0.05% $NaN_3$, 0.1% BSA pH 7.4.

An aliquot (0.1 ml) from each dilution of antibody was mixed with 0.1 ml (15,000 cpm) of [$^3$H]T-2 in 0.01M sodium phosphate 0.9% NaCl, 0.05% $NaN_3$, 0.1% BSA pH 7.4. The tubes were incubated for 2 hr at 37° C., then cooled to 0° C. One ml of ice cold charcoal solution was added and the tubes were vortexed for 30 sec, then placed on ice for 3 min. After centrifugation at 1700×g for 1.5 min at 0° C., 0.5 ml of the supernatant was pipetted into counting vials containing 3.5 ml of scintillation fluid (Scinti Verse II; Fisher). The samples were counted for 5 min each in a Packard Tricarb 4530 scintillation counter. The antibody titer was determined by plotting the antibody dilution versus the percent of radioactivity bound by that dilution. The titer of the T-2 antibody was found to be 1:100.

Determination of dissociation rate constant of T-2 antibody

Affinity purified T-2 antibody (1.2 ml; 0.26 mg) was mixed with 1.2 ml (180,000 cpm) [$^3$H]T-2 in 0.01M $NaH_2PO_4$, 0.9% NaCl, 0.1% BSA, 0.05% $NaN_3$ pH 7.4 and incubated overnight at 4° C. After cooling to 0° C., a 0.2 ml sample (0 time) of the above mixture was mixed with 0.2 ml dextran coated charcoal (prepared as previously described), and incubated at 0° C. for 10 min. Then the charcoal was removed from the solution by pushing the fluid through 0.45 μm HA filters (Millipore) with a syringe. A 10,000 fold excess of nonradioactive T-2 was added to the antibody and [$^3$H]T-2 mixture. This solution was vortexed, 0.2 ml samples were taken at 20 sec, 90 sec, 2 min, 4 min, 6 min and 15 min, and the samples were treated in the same manner as the 0 time sample. Seven hundred microliters of each sample solution were pipetted into 10 ml of scintillation cocktail. All samples were then counted for 5 min. The dissociation rate constant for T-2 antibody was determined by plotting time vs. log of percent binding using the 0 time sample as 100% binding, and found to be $4.62 \times 10^{-3}$ sec$^{-1}$, which corresponds to a half-life of 150 seconds.

Analysis of T-2 using an equilibrium assay with affinity separation

Ten microliters of T-2 toxin standards at concentrations of 0, 0.1, and 1.0 μg (0, 0.21, and 2.1 nmol) were mixed with 0.2 ml (2.38 nmol) of Fab'-RNase conjugate. This mixture was incubated for 30 min at room temperature after which it was applied to a column containing 0.1 ml of T-2 affinity gel. The column bed (0.5×5 cm) was immediately washed with 0.1M TRIS HCl pH 7.5 and eluted with a solution of T-2 (1 mg/ml) in the same buffer at a flow rate of 0.25 ml/min. Fractions (1.2 ml) were collected and the RNase activity in each was determined with the polymeric substrate assay previously described.

Analysis of T-2 by Affinity Chromatography with Fab'-fluorescein

With the necessary reagents prepared and characterized, an analysis for T-2 by the "hit and run" affinity chromatography technique (FIG. 2) was performed. A T-2 "hit-and-run" column was packed and conjugate was loaded as described below. Samples of T-2 (0–50 ng) were applied to the column. After incubation, the amount of fluorescence, due to the release of Fab'-fluorescein was measured (FIG. 6). Using this method, 1 ng of T-2 could be detected. A representative standard curve is shown in (FIG. 7). Importantly, all of the data shown in the latter figure, arising from 20 assays, were done successively on the same Fab'-fluorescein T-2 hit-and-run column, including a repetition of the 50 ng dose of T-2 at the end of the assay sequence.

A 1 ml Supelclean (Supelco) filtration column was packed with 0.20 ml of T-2 affinity gel. The column was equilibrated with 10 ml of 0.01M TRIS HCl pH 7.5. One ml ($A_{280}$=0.8/cm) of Fab'-fluorescein conjugate was loaded onto the column at a flow rate of 0.1 ml/min. This was followed by washing with equilibration buffer at a flow of 0.3 ml/min while monitoring fluorescence by means of a Schoeffel FS970 fluorometer (480 nm excitation; 520 nm emission filter). Washing was terminated when the fluorescence signal returned to preloading levels. Samples of T-2 (0, 1, 5, 10, 25, and 50 ng) in 0.2 ml of 0.01M TRIS HCl pH 7.5 were applied to the column at room temperature at a flow rate of 0.68 ml/min. Once the sample completely entered the gel bed the flow was stopped for 5 min. At the end of this incubation period, released conjugate was eluted with 0.01M TRIS HCl pH 7.5 and the fluorescence signal was measured as just described.

Unsuccessful Analysis of T-2 using an equilibrium assay with affinity separation Samples of T-2 were mixed with excess Fab'-RNase, and this mixture was incubated and then applied to a T-2 affinity column for separation of bound from free conjugate. Conjugate that is complexed with soluble T-2 will not bind to the immobilized T-2 on the affinity gel and therefore will elute in the wash fractions. Thus, the more T-2 that is present in a sample the more enzyme activity that will elute unretained. In our hands, however, this assay system was not successful. High concentrations of RNase activity were present in the unretained fractions even in the absence of T-2, and as a result we were unable to quantitate T-2 even at the 1.0 μg level.

Analysis of T-2 by affinity chromatography using Fab'-RNase conjugate

A T-2 affinity column was packed and loaded with Fab'-RNase as described below. Samples (0–3000 ng) of T-2 were applied to the column. Fractions were collected and the total amount of RNase activity eluted was measured by the polymeric substrate analysis previously described. One hundred nanograms of T-2 could be detected using this method as shown in FIG. 8.

A T-2 affinity column was packed, loaded with 1 ml ($A_{280}$=0.8) of Fab'-RNase conjugate, and washed in the same manner as described for the Fab'-fluorescein conjugate. The absorbance at 280 nm was monitored and washing was stopped when it returned to baseline levels. Samples of T-2 (0, 100, 250, 500, 1000, and 3000 ng), in 0.2 ml of 0.01M TRIS HCl pH 7.5, were applied to the column at a flow rate of 0.68 ml/min. The flow was stopped and, after a 5 min incubation, released conjugate was eluted with buffer. Fractions were collected and the amount of eluted RNase activity was determined.

Preparation of Fab'-fluorescein-biotin

Fab'-fluorescein ($2.8\times10^{-8}$ mole), in 0.1M $K_2HPO_4$ pH 7.5, was mixed with 100 μl of DMSO containing Biotin-X-NHS ($2.9\times10^{-7}$ mole). This mixture was incubated overnight on a Nutator at room temperature. Unreacted biotin was removed by gel filtration on a PD-10 column. The product was characterized by determining binding to avidin and T-2.

Preparation of avidin agarose

Two milliliters of Affi-Gel 10 were washed with 6 ml of cold water, and 1 ml of avidin solution (4 ng/ml) was added. The gel was incubated overnight on a Nutator at room temperature, after which the avidin solution was removed and the gel was washed with 10 vols of 0.1M $K_2HPO_4$ pH 7.5 and 10 vols of 6M guanidine HCl pH 1.5. The presence of avidin was established by reaction of the gel with HABA dye.

Determination of Fab'-fluorescein-biotin binding to avidin and T-2

Avidin binding: A column (0.5×1 cm) was packed with avidin agarose. The column was equilibrated with 0.1M $K_2HPO_4$ pH 7.5. Two hundred microliters (0.8 $A_{280}$/ml) of Fab'-fluorescein or Fab'-fluorescein-biotin were applied to the column. The column was washed with 10 ml of 0.1M $K_2HPO_4$ pH 7.5, and then eluted with 10 ml of 6M guanidine HCl pH 1.5. The amount of fluorescence in the eluted fraction was monitored as previously described.

Figure 9:
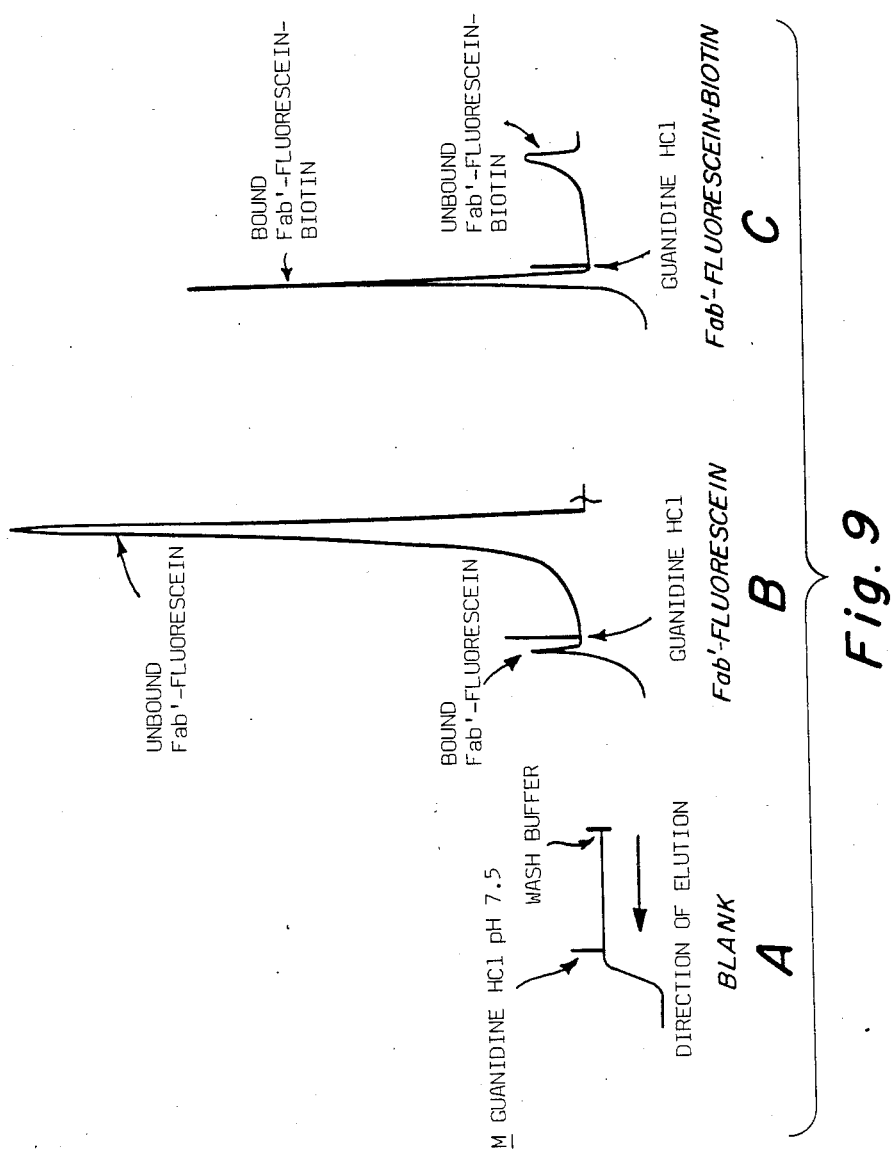
FIG. 9 demonstrates the amount of Fab'-fluorescein-biotin bound to an avidin column, in comparison to Fab'-fluorescein as standard.

FIG. 9 depicts the amount of Fab'-fluorescein-biotin bound to an avidin agarose column vs. Fab'-fluorescein as a standard. It can be seen that the major portion of Fab'-fluorescein conjugate is not bound to the avidin column but elutes with the wash buffer (0.1M $K_2HPO_4$, pH 7.5). The major portion of the Fab'-fluorescein-biotin conjugate binds to the avidin column and is eluted with 6M guanidine HCl pH 1.5.

Figure 10:
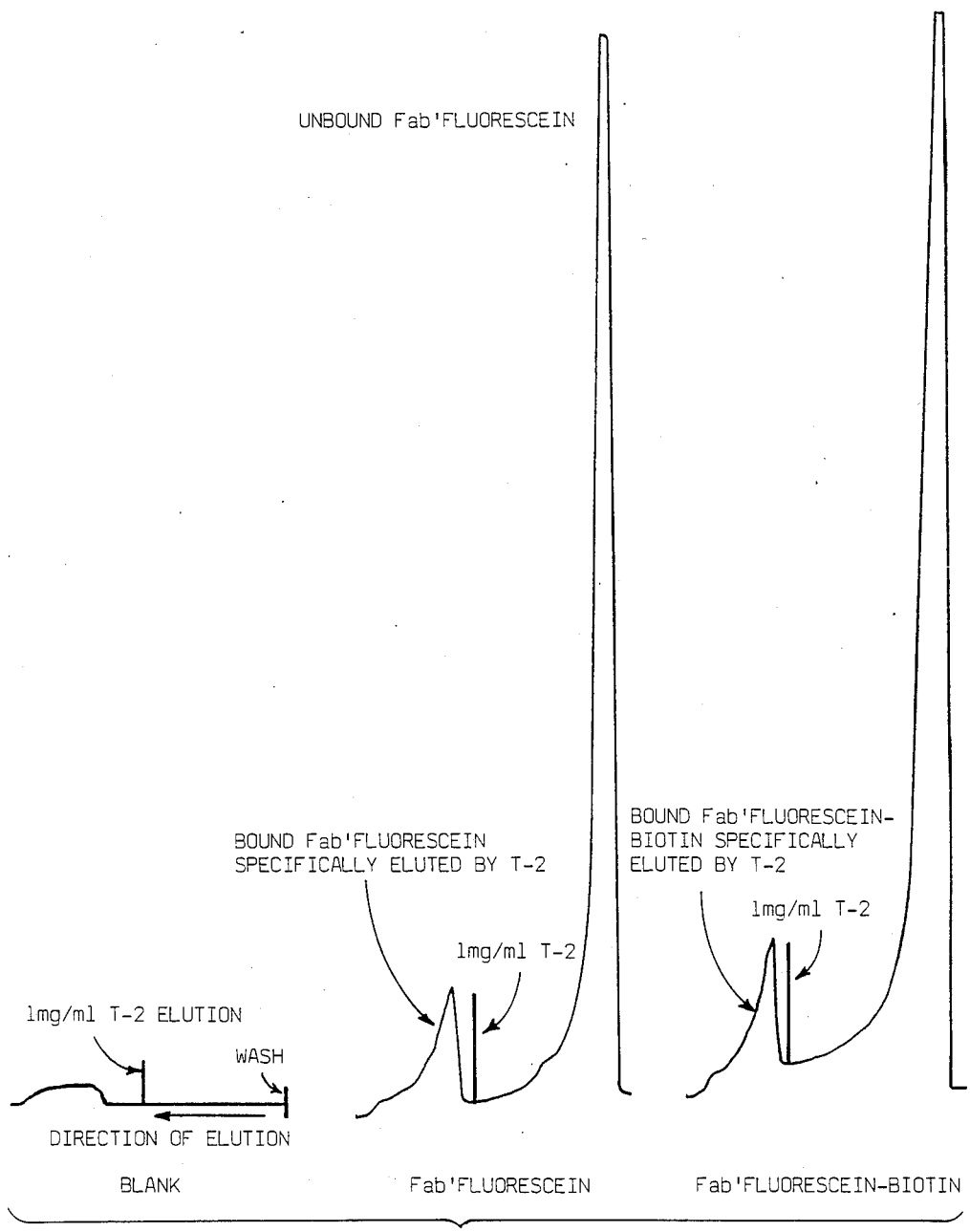
FIG. 10 demonstrates the amount of Fab'-fluorescein-biotin bound to a T-2 affinity column, in comparison to Fab'-fluorescein as standard.

T-2 binding: The ability of Fab'-fluorescein-biotin to bind to T-2 was determined in comparison to Fab'-fluorescein using a T-2 affinity column. A 1 ml Supelclean (Supelco) column was packed with 200 μl of T-2 affinity gel. The gel bed (0.5×1 cm) was equilibrated with 10 mM Tris HCl pH 7.5. One hundred microliters (0.8 $A_{280}$/ml) of Fab'-fluorescein or Fab'-fluorescein-biotin were applied to the column. After five minutes of incubation at room temperature, the column was washed with 10 vols of 10 mM Tris HCl pH 7.5. The column was eluted with a 1 mg/ml T-2 solution in the same buffer but with 5% methanol. The amount of fluorescence in the eluent was monitored as previously described. The chromatographic patterns for Fab'-fluorescein-biotin and Fab'-fluorescein were essentially the same, as seen in FIG. 10, demonstrating that the binding characteristics of Fab'-fluorescein-biotin for T-2 are intact.

"Hit-and-Run" Immunoassay for T-2 using Fab'-fluorescein-biotin conjugate

The analysis for T-2 using Fab'-fluorescein-biotin conjugate was identical to that described above with the fluorescein conjugate except a 100 ng standard was run as well, and the column was loaded with 1 ml (0.8 $A_{280}$/ml) of Fab'-fluorescein-biotin conjugate.

A T-2 "hit-and-run' column was packed and loaded with Fab'-fluorescein-biotin as described above. Samples of T-2 (0–100 ng) were applied to the column, and the amount of Fab'-fluorescein-biotin released after incubation was measured by its fluorescence using a flow-through spectrofluorometer. The data obtained for this conjugate was similar to that shown previously for the Fab'-fluorescein conjugate.

Preparation of T-2 BSA conjugate

T-2 tresyl ester (12 mg; 0.02 mmol) in 0.5 ml DMSO was added to 5 ml of a solution of BSA (44.6 mg; 0.66 μmol) in 0.1M potassium phosphate pH 7.2. DMSO was added to give a final DMSO/buffer ratio of 4:1. The reaction mixture was stirred for 48 hr at 4° C., dialyzed at 4° C. vs 4×4 l of distilled water, and lyophilized.

Figure 11:
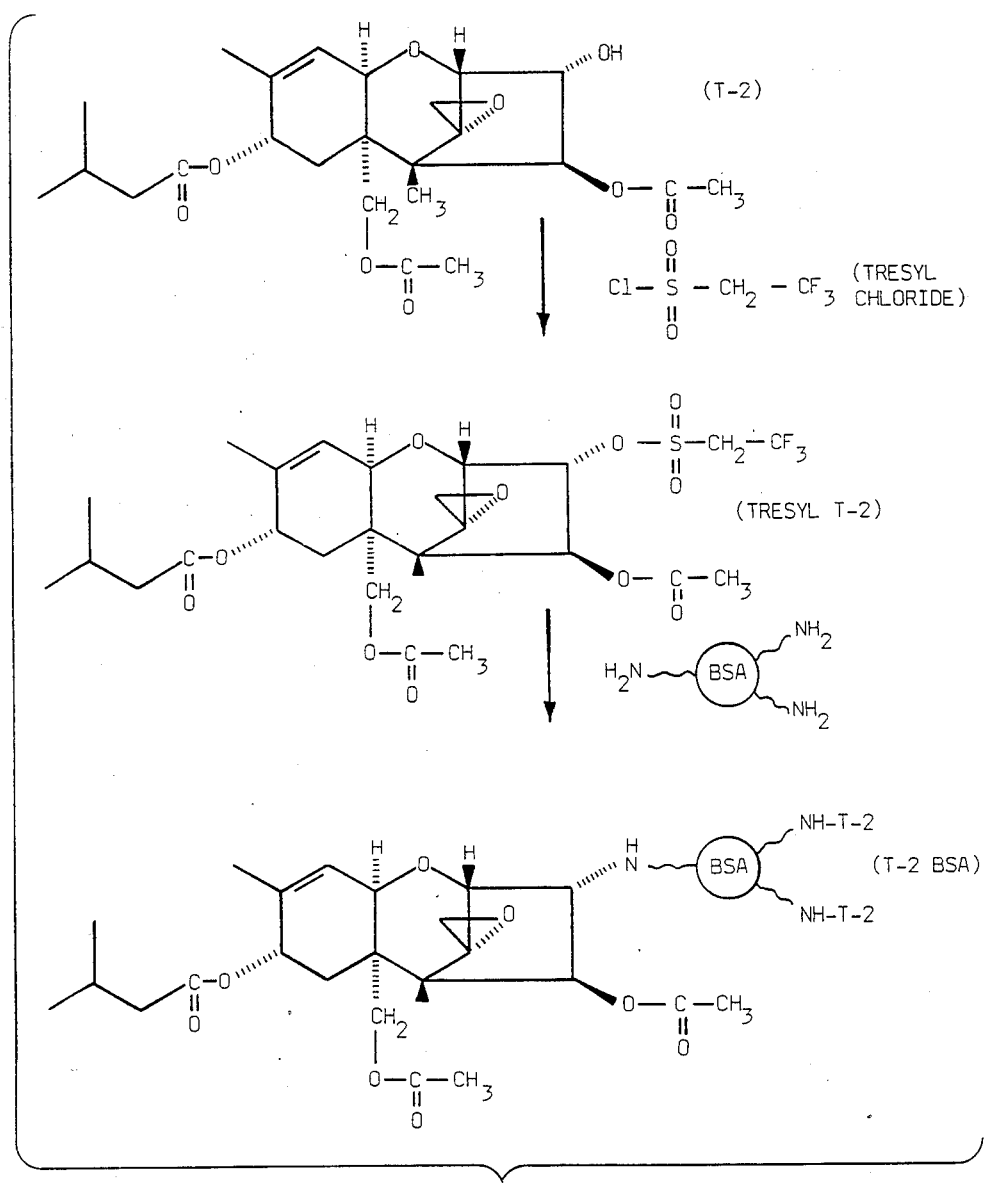
FIG. 11 is a schematic showing preparation of a T-2 toxin BSA-conjugate.

The reaction of BSA with T-2 tresyl ester (FIG. 11) resulted in the incorporation of 8 T-2 molecules per molecule of protein (average value). The content of T-2 was determined by calculating the amount of radioactivity bound per mole of BSA and the concentration of BSA was based on its absorbance at 280 nm ($E=4.24\times10^4$ mol cm$^{-1}$). Increasing the T-2:BSA ratio in the initial reaction mixture gave rise to insoluble or sparingly soluble products.

Stability of T-2 BSA conjugate

The stability of the T-2 BSA conjugate was investigated by dialyzing the conjugate against 0.01M potassium phosphate buffers ranging in pH from 4–10. The number of counts of [$^3$H]T-2 inside and outside the dialysis bag was determined after 5 and 10 days. In addition, the absorbance at 280 nm inside the bag was measured, and the radioactivity to protein ratio determined. The T-2/BSA ratios inside the dialysis bag after 5 to 10 days at pH 4, 7, 8, or 10 are shown in Table II. The results show little or no hydrolysis of the conjugate even at pH 10.

TABLE II

Stability of T-2 Toxin BSA Conjugate by Dialysis Against Buffers Ranging From pH 4–10 for 5–10 Days

| pH | Days of Dialysis | |
|----|---|---|
|   | 5 mols of T-2/1 mol BSA | 10 mols of T-2/1 mol BSA |
| 4 | 8.8 | 8.2 |
| 7 | 8.8 | 8.1 |
| 8 | 7.9 | 7.5 |
| 10 | 7.7 | 8.2 |

Coupling of BSA-T-2 to Affi-Gel 15

Twenty-one ml of Affi-Gel was drained of isopropyl alcohol and washed 3 times with DMSO. To the above gel was added BSA-T-2 solution (9.4 mg in 16 ml DMSO) and the mixture was stirred at room temperature for 48 hr. The gel was washed 3 times with DMSO and the unreacted ester was blocked with 20 ml of 1M ethanolamine washing 3 times for 1.5 hr. The reaction was followed by measuring absorbance at 260 nm until no more ester was detected. The gel was washed with buffer (KPB, 1M, pH 7.2) and stored in this solvent at 4° C. The concentration of the T-2 on the gel was ≧0.016 μmole/1 ml of gel which was determined by its radioactivity (specific activity of BSA-T-2 is 8 mmole T-2/mmol BSA.)

Reaction of T-2 tresyl ester with hexylamine Sepharose gel

Four milliliters of hexylamine Sepharose gel (6–10 μmole of amino groups/ml of gel) was washed with 0.5M NaCl, distilled water and DMSO/0.1M KPB, pH 7.2 (70/30(v/v)). To the above gel T-2 tresyl ester solution (40 μmol in 3.9 ml of DMSO-buffer(70/30)) was added and the reaction stirred at 4° C. for 18 hr after which the gel was washed with DMSO/buffer (70/30), MeOH/buffer (70/30) and finally washed with buffer. Twenty μl of the gel was counted which yielded 0.32 μmole T-2/1 ml of gel.

Preparation of T-2 benzoylhydrazine

T-2 tresyl ester (14 mg, 0.03 mmol) in 1.5 ml of DMSO/buffer (0.01M potassium phosphate, pH 7.15, 70/30(v/v)) was added to 0.5 ml of benzoylhydrazine solution (11.66 mg, 0.09 mmol) in the same solvent. The reaction mixture was stirred under $N_2$ at room temperature for 48 hrs and was followed by TLC (toluene:ethyl acetate:formic acid (6:3:1)). The T-2 tresyl spot disappeared and a faster moving spot appeared. The reaction mixture was poured onto water and the product was extracted into ethyl acetate. The organic layer was washed with water and dried over anhydrous $Na_2SO_4$. Purification was done by preparative TLC (ethyl acetate/hexane (50/50)) which yielded 13 mg of T-2 benzoylhydrazine (77% yield). The structure was confirmed by spectral analysis.

Reaction of epoxy silica gel with adipic acid dihydrazide and coupling to T-2 tresyl ester Adipic acid dihydrazide (30.88 ng, 177 μmol) was dissolved in 2 ml of 1M KPB pH 7.3 and added to 250 μg of epoxy silica gel (71 μmol epoxy/gm of gel, Beckman) suspended in 0.5 ml of the same buffer. The suspension was stirred at room temperature for 72 hrs. After this time the gel was washed with 0.1M KPB pH 7.3 until no more free amine could be detected in the wash solution as indicated by the absence of a red color upon the addition of 3% TNBS. A sample of washed gel was also treated for the presence of amine groups by means of the TNBS spot test in which a small amount of gel was suspended in saturated sodium borate buffer pH 9.3 and 3% TNBS was added. The appearance of a dark red color on the gel showed the presence of covalently linked adipic acid hydrazide. T-2 tresyl ester (41 μmol, specific activity 35 cpm/μg) dissolved in 4 ml of DMSO/0.1M KPB pH 7.3 (70/30) was added to the remaining gel and the suspension was stirred at room temperature for 48 hrs. The gel was then washed with DMSO/buffer (70/30), MeOH/buffer (30/70), and buffer. After washing, the gel was stored in 1M KPB at pH 6.5. A sample of gel (50 μl) was suspended in 4 ml of scintillation cocktail and counted. The concentration of T-2 bound to the gel was calculated from the cpm and determined to be ≧2.5 μmol/ml of gel.

The above synthesis is one example of the synthesis of a hydrazide silica useful in the preparation of conjugates of silica and analytes. More generally, silica possessing epoxy functional groups, e.g., 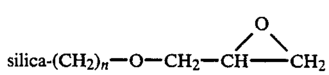 where n is a number from 1 to 10 (preferably 3–6), reacts under the above conditions with carbohydrazide ($H_2NNH—CO—NHNH_2$) or with dihydrazides $H_2N—NH—CO—(CH_2)_m—CO—NHNH_2$ where m is a number from 1 to 10, to yield hydrazide silica having the generalized formulae 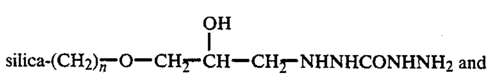 and 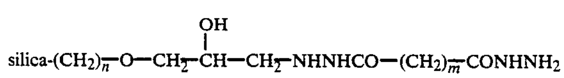 where n is a number from 1 to 10 and m is a number from 1 to 10.

Poor performance of T-2 hexylamine Sepharose and T-2 BSA Affi-Gel 15 affinity chromatography columns While antibody was retained on the T-2 hexylamine Sepharose column, it could not be eluted either by the addition of T-2 to the column or with a low pH mobile phase. A control experiment with hexylamine Sepharose, not modified with T-2, gave the same result. Thus the antibody was nonspecifically and strongly bound to this packing, precluding the use of a T-2 hexylamine Sepharose column for affinity purification of the antibody. This column was therefore not suitable for use as a hit-and-run column for assay of T-2.

The performance of the T-2 BSA Affi-Gel 15 column for purification of antibody was also unsatisfactory. Using T-2 BSA Affi-Gel 15, only 14 to 29% of the bound antibody could be eluted by the addition of a 20 fold excess of T-2 to the column. Antibody also could not be eluted with 0.1M TRIS, 4.5M $MgCl_2$, pH 7.5. Thus, once again significant nonspecific binding of the antibody seemed to be taking place on this column. Also the amount of antibody eluted with excess T-2 was variable. A T-2 BSA Affi-Gel 15 column therefore was neither attractive for purifying T-2 antibody, nor for use in a hit-and-run immunoassay for T-2.

Example 1: Fluorescein-divalent antibody/T-2 tresyl polyacrylamide

1. T-2 antibody-fluorescein conjugate is prepared by reaction of T-2 antibody with fluorescein isothiocyanate at pH 9.3.

2. Aminoethyl Bio Gel P2 (Bio Rad) is reacted with succinic anhydride, and then with adipic acid dihydrazide in the presence of EDAC (Bio Rad), forming polyacrylamide adipic acid hydrazide.

3. T-2 toxin is reacted with 6 equivalents of 2,2,2-trifluoroethanesulfonyl chloride in acetone/pyridine, forming T-2 tresyl ester.

4. Adipic acid hydrazide polyacrylamide is reacted with T-2 tresyl ester in DMSO/buffer pH 7.2 (70/30) to form T-2 polyacrylamide.

5. Fluorescein-T-2 antibody is mixed with T-2-polyacrylamide, followed by washing with buffer at pH 7.5 to remove unreacted antibody, forming T-2 antibody-fluorescein-T-2 polyacrylamide complex.

6. Addition of extrinsic T-2 to this complex releases fluorescein T-2 antibody and the eluted fluorescence is measured by a flow-through fluorescence detector.

7. Alternatively, a DAS antibody may be substituted for T-2 antibody in step 1, giving a DAS antibody-fluorescein conjugate; a DAS tresyl ester is prepared in step 3 and converted to DAS-polyacrylamide in step 4; the DAS antibody-T-2 conjugate is mixed with the DAS-polyacrylamide in step 5 providing a DAS antibody-fluorescein-DAS-polyacrylamide complex; and in step 6 addition of extrinsic DAS to this complex releases fluorescein-DAS antibody for determination of DAS.

Example 2: Fab'-β-galactosidase/T-2 agarose

1. T-2 monoclonal antibody is digested with pepsin, the $(Fab')_2$ fragment is reduced with mercaptoethylamine, and the sulfhydryl groups of the resulting Fab' fragments are capped with iodoacetamide according to a standard protocol (Freytag, J. W., Clin. Chem. 30 (1984) 1494), producing protected Fab'.

2. The protected Fab' is reacted with GMBS to produce maleimido-Fab'.

3. β-galactosidase is reacted with the maleimido-Fab', forming Fab'-β-galactosidase.

4. Affi-Gel 10 agarose gel (Bio Rad) is reacted with diaminooctane (DAO), followed by reaction with T-2 tresyl ester (prepared as described in example 1), and capping with ethanolamine, forming T-2-agarose.

5. Fab'-β-galactosidase conjugate is mixed with T-2-agarose, followed by washing with buffer to remove unreacted conjugate, forming Fab'-β-galactosidase T-2 agarose complex.

6. Addition of extrinsic T-2 to the Fab'-β-galactosidase-T-2-agarose complex release Fab'-β-galactosidase for detection by its enzymatic activity with o-nitrophenylgalactoside as the substrate.

7. Alternatively, in step 4 T-2 tresyl ester is immobilized on thiopropyl sepharose 6b (pharmacia), which possesses a reactive sulfhydryl group, forming T-2-agarose with a sulfur atom in the leash; in step 5 this is mixed with Fab'-β-galactosidase and T-2 is determined as in step 6.

8. Alternatively, adipic acid dihydrazide is substituted for DAO in step 4.

Example 3: Fab'-fluorescein/digoxin-silica

1. A monoclonal antibody is obtained by immunizing mice with digoxin-BSA conjugate following a standard protocol (Goding, J. W., *Monoclonal Antibodies: Principles and Practices*, Academic press, N.Y., 1983).

2. Fab'-fluorescein is produced according to the procedure described in example 1 except starting with an anti-digoxin antibody.

3. Digoxin is treated with sodium periodate, forming oxidized digoxin.

4. The oxidized digoxin is reacted with ethylenediamine in the presence of sodium cyanoborohydride, forming amino-digoxin.

5. Amino-digoxin is reacted with epoxy activated silica, forming digoxin-silica; alternatively, amino-digoxin can be reacted with tresyl activated 2,3-dihydroxypropyl silica (Pierce) to form digoxin-silica; alternatively, oxidized digoxin is reacted with hydrazide silica (prepared as described in example 6), forming digoxin-silica.

6. Fab'-fluorescein is mixed with digoxin-silica to form a Fab'-fluorescein digoxin-silica complex.

7. Addition of extrinsic digoxin to the complex releases Fab'-fluorescein which is measured in a flow-through fluorescence detector.

Example 4: Fab'-HRPO/T4 Immobilon Membrane

1. T4 (thyroxine hormone) monoclonal antibody and its maleimido-Fab' fragment are produced as described in example 2, except T4-BSA is used as the immunogen.

2. Horseradish peroxidase (HRPO) is lightly modified with SPDP active ester, forming SPDP-HRPO that retains considerable enzymatic activity.

3. SPDP-HRPO is reduced with one equivalent of dithiothreitol, forming sulhydryl-HRPO, that is in turn reacted with maleimido-Fab', forming Fab'-HRPO conjugate.

4. Immobilon membrane is reacted with 1,6-hexanediamine, followed by quenching with ethanolamine, forming aminohexyl-Immobilon membrane.

5. Thyroxine is reacted with acetic anhydride, forming N-acetylthyroxine, which in turn is immobilized onto aminohexyl Immobilon membrane by means of the carbodiimide method (Rich, P. H. and Singh, J., *The Peptides*, 1, (1979) 241–261) forming Acetyl-T4-Immobilon membrane.

6. Alternatively, Immobilon membrane is reacted with ε-amino caproic acid, followed by activation to an NHS ester, forming NHS-Immobilon membrane, and T4 or acetyl-T4 is reacted with NHS-Immobilon membrane to form T4-Immobilon membrane or acetyl-T4 Immobilon membrane.

7. Acetyl-T4-Immobilon membrane or T4-Immobilon membrane is reacted with Fab'-HRPO conjugate to form Acetyl-T4 (or T4)-Immobilon membrane-Fab'-HRPO complex, with unreacted Fab'-HRPO being removed by washing with buffer.

8. Addition of extrinsic T4 in a stream or by diffusion to either complex releases Fab'-HRPO, which is detected by measuring the enzymatic activity of released HRPO.

Example 5: [$^{125}$I] Fab'/Insulin-Nylon Tube

1. Insulin monoclonal antibody and protected Fab' fragment are prepared as described in example 2 except insulin is used as the immunogen.

2. Nylon capillary tubing is activated by hydrolysis in 3M HCl, washing with water, and treatment with glutaraldehyde as described (Sundaran, P. V., Igloi, M. P., Wasserman, R., Hinsch, W. and Knoke, K. J., *Clin. Chem.*, 24 (1978) 234–239).

3. Protected Fab' is reacted with [$^{125}$I] Bolton Hunter reagent at pH 8.0, forming [$^{125}$I] Fab'.

4. Insulin is reacted with activated nylon tubing, followed by quenching of unreacted glutaraldehyde with aqueous ethanolamine, forming nylon-immobilized insulin.

5. [$^{125}$I] Fab' through the nylon tube, followed by washing away unreacted [$^{125}$I] Fab' with buffer, forming [$^{125}$I] Fab' insulin-nylon.

6. Addition of extrinsic insulin to the complex releases [$^{125}$I] Fab' from the nylon tube, which is measured by a flow-through radioactivity detector.

Example 6: Fab'-isoluminol/T-2-silica

1. Anti T-2 Fab' is reacted with N-succinimidyl 3-(2-pyridyldithio)propionate (SPDP) forming SPDP-Fab'.

2. Aminobutylethyl isoluminol, prepared as described (Schroeder, H. R. and Yeager, F. M., *Anal. Chem.*, 50, (1978) 1114) is reacted with GMBS to form maleimido-isoluminol.

3. SPDP-Fab' is reduced with dithiothreitol, forming sulfhydryl-Fab', followed by reaction with maleimido-isoluminol, forming Fab'-isoluminol.

4. Epoxy-silica (Beckman) is reacted with adipic acid dihydrazide in 1M potassium phosphate buffer, pH 7.3, for 3 days at room temperatue on a nutator, giving hydrazide-silica.

5. Hydrazide-silica is reacted with T-2 tresyl ester in 70% DMSO/30% 0.01M phosphate buffer pH 7.2 for 48 hr at room temperature, forming T-2-silica.

6. Fab'-isoluminol is reacted with T-2-silica followed by washing with buffer pH 7.5, forming Fab'-isoluminol-T-2-silica complex.

7. Extrinsic T-2 is added to this complex causing the release of Fab'-isoluminol.

8. Aliquots of the released Fab'-isoluminol are detected by their chemiluminescence as described (Messeri, G., et al, *Clin. Chem.*, 30 (1984) 653).

Example 7: Fab'-isoluminol/E$_2$-silica

1. Anti-E$_2$ (estradiol-17β) monoclonal antibody is prepared as described in example 2 using an E$_2$-BSA conjugate prepared as described (Roda, A. and Belelli, G. F., *J. Ster. Biochem.*, 13 (1980) 449).

2. Anti-E$_2$ Fab'-isoluminol is prepared as described for Anti T-2 Fab'-isoluminol in example 6.

3. E$_2$ hemisuccinate is prepared as described (Messeri, G., *Clin. Chem.*, 30 (1984) 653), activated with a water soluble carbodiimide, and coupled to hydrazide silica (prepared as described in example 6), forming E$_2$-silica.

4. E$_2$-silica is complexed with Anti E$_2$ Fab'-isoluminol, followed by washing, forming Anti E$_2$ Fab'-isoluminol E$_2$ silica complex.

5. When this complex is treated with E$_2$, Fab'-isoluminol is eluted that is detected by its chemiluminescence as described in example 6.

Example 8: Fab'-dye/DAS glass

1. Fab' recognizing DAS (diacetoxycrirpenol toxin) prepared as previously described for Fab' anti T-2 (starting with DAS-BSA immunogen prepared as described below) is reacted with triazine dye at pH 8, forming Fab'-dye conjugate.
2. Glass particles are converted to amino-glass using β-aminopropyltriethoxysilane as described (Robinson, P. J., Dunhill, P. and Lilly, M.D., *Biochem. Biophys. Acta*, 242 (1971) 659–661).
3. Amino glass is activated with glutaraldehyde as described (Robinson, P. J. ibid.), giving glutaraldehyde-glass.
4. DAS tresyl (prepared as described for T-2 tresyl) is reacted with BSA, forming DAS-BSA conjugate.
5. DAS-BSA is reacted with glutaraldehyde glass, forming DAS-glass.
6. Alternatively, glutaraldehyde glass is reacted with BSA or adipic acid dihydrizide, followed by reaction with DAS tresyl ester, followed by quenching of unreacted glutaraldehyde sites with ethanolamine, forming DAS glass.
7. Fab'-dye is reacted with DAS-glass, followed by washing with buffer pH 7.5 to remove any unreacted Fab'-dye, forming Fab'-dye DAS glass complex.
8. Addition of extrinsic DAS releases some Fab'-dye conjugate, and the amount of dye released is measured by its absorbance.

Example 9: Fab'-fluorescein/DHT-silica

1. DHT (dihydrotestosterone steriod hormone) is converted to its corresponding bis-(thioethyl) ketal by reaction with triethylthioborate ($B[SCH_2CH_3]_3$), forming DHT-TEK.
2. DHT-TEK is activated with tresyl chloride and coupled to hydrazide-silica (prepared as described in example 6), followed by removal of the two thioethyl groups with mercuric chloride/cadmium carbonate in aqueous acetone, forming DHT-silica.
3. Succinyl-DHT is prepared as described (Mickelson, K. E., Teller, D. C., and Petra, P. H., *Biochem.*, 17, (1978), 1409–1415), and coupled to BSA using a water-soluble carbodiimide, giving DHT-BSA.
4. A monoclonal antibody is prepared for DHT using DHT-BSA, and an anti-DHT Fab'-fluorescein is prepared as described in the EXPERIMENTAL SECTION for anti T-2 Fab'-fluorescein.
5. DHT-silica is complexed with anti-DHT Fab'-fluorescein, followed by washing, forming anti DHT Fab'-fluorescein DHT-silica complex.
6. When this complex is treated with DHT, Fab'-fluorescein is specifically eluted that is detected by its fluorescence.

Example 10: Virus/Polyacrylamide

1. Adipic acid hydrazide polyacrylamide is prepared as in example 1, and rected with glutaraldehyde, forming glutaraldehyde-polyacrylamide.
2. A virus is reacted with glutaraldehyde polyacrylamide, followed by quenching with ethanolamine, forming virus-polyacrylamide.
3. A monoclonal Fab'-fluoresceine is prepared against the virus by standard techniques, and reacted with the virus-polyacrylamide, forming a Fab'-fluorescein-virus-polyacrylamide complex.
4. Addition of extrinsic virus of Fab'-fluorescein-virus-polyacrylamide complex releases Fab'-fluorescein and the eluted fluorescein is detected.
5. Alternatively, the Fab' is labeled with a release tag (Giese, R. W., *Trends in Anal. Chem.* 2 (1983) 166–168, forming Fab'-release tag-virus-polyacrylamide complex that elutes Fab'-release tag when exposed to extrinsic virus in a stream, by diffusion or by electrophoretic migration.

6. Alternatively, the virus is immobilized on Sepharose 2B or Trisacryl by activating these substrates with tresyl chloride following by reaction with the virus, forming virus-Sepharose 2B or virus-Trisacryl, which is used in place of virus-polyacrylamide in the above steps 3-5.

References

1. Bamburg, J. R., Strong, F. M., in "Microbial Toxins," Vol. VII, S. Kadis, A. Ciegler, S. J. Ajl, Eds., pp. 207-292, Academic Press, New York, 1971.
2. Bamburg, J. R., in "Mycotoxins and Other Fungal Related Food Problems," Rodricks, Ed., pp. 144-161, Am. Chem. Soc., Washington, D.C., 1976.
3. Robb, J., and Norval, M., Applied and Environmental Microbiology, 46 (1983), 948-950.
4. Ueno, Y. (1980), Adv. Nutr. Res. 3, 301.
5. Bamburg, J. R., Clinical Toxicology, 5 (1972), 495-515.
6. Eppley, R. M., J. Assoc. Off. Anal. Chem., 58 (1975), 906-908.
7. Scott, P. M., J. Assoc. Off. Anal. Chem., 4 (1982), 876-883.
8. Bata, et. al., J. Assoc. Off. Anal. Chem., 66 (1983), 577-581.
9. Chaytor, J. P. and Saxby, M. J., J. Chromatography, 237 (1982), 107-113.
10. Chu, F. S., J. Food Protection, 7 (1984), 562-569.
11. Swanson, S. P., et. al., J. Assoc. Off. Anal. Chem., 66 (1983), 909.
12. Fontelo, P. A., Beheler, J., Bunner, D. L., and Chu, F. S., Applied and Environmental Microbiology, 45 (1983), 640-643.
13. Chu, F. S., Grossman, S., Wel, R. D., and Mirocha, C. J., Applied and Environmental Microbiology, 37 (1979), 104-108.
14. Hunter, K. W., Brimfield, A. A., Miller, M., Finkelman, F. D., and Chu, S. F., Applied and Environmental Microbiology, 49 (1985), 168-172.
15. Freytag, J. W., Dickinson, J. C., and Tseng, S. Y., Clin. Chem., 30 (1984), 417-420.
16. Freytag, J. W., Lau, H. P., and Wadsley, J. J., Clin. Chem., 30 (1984), 1494-1498.
17. Lowry, O. H., Rosebrough, N. J., Farr, A. L., and Randall, R. J., J. Biol. Chem., 193 (1951), 265.
18. Snyder, S. L. and Sobocinski, P. Z. Anal Biochem, 64 (1975), 284-288.
19. Sedlak, J. and Lindsay, R. H., Anal Biochem, 25 (1968) 192.
20. Lowry, O. H., et al J. Biol. Chem., 193 (1951) 265-275.
21. Bio Rad Bulletin, 1172, Bio Rad Chemical Division, Richmond, CA.
22. The, T. H. and Feltkamp, T. E. W. Immunol, 18 (1970) 865-873.
23. Smith, P. K., et al Anal Biochem, 150 (1985) 76-85.

What is claimed is:

1. A hydrazide silica having the formula

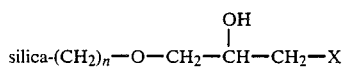
where
X is —NHNHCONHNH$_2$ or —NHNHCO(CH$_2$)$_m$CONHNH$_2$ and n and m are numbers between 1 and 10.
2. A hydrazide silica of claim 1 wherein n is a number from 3 to 6.
3. A hydrazide silica of claim 2 wherein m is 4.
* * * * *

UNITED STATES PATENT AND TRADEMARK OFFICE
CERTIFICATE OF CORRECTION

PATENT NO. : 4,801,726

DATED : January 31, 1989

INVENTOR(S) : Roger W. Giese, et al.

It is certified that error appears in the above-identified patent and that said Letters Patent is hereby corrected as shown below:

```
In Column 1, line 35, "Fusarium" should read --Fusarium--.
In Column 1, line 55, "Further," should read --furthermore--.
In Column 1, line 67, "varity" should read --variety--.
In Column 3, line 11, "as radioisotope" should read --as a
     radioisotope--.
In Column 3, line 39, "protein T-2" should read --protein-T-2--.
In Column 3, line 43, "in vivo" should read --in vivo--.
In Column 7, line 40, "attached:" should read --attached;--
In Column 8, line 56, "N-" should read --N--.
In Column 9, line 44, "complex" should read --complexes--.
In Column 10, line 4, "applicatin" should read --application--.
In Column 10, line 37, "absorbs" should read --adsorbs--.
In Column 11, line 25, "fo" should read --for--.

In Column 15, line 33, "mercaptoe-" should read --mercapto- --.
In Column 15, line 34, "thylamine" should read --ethylamine--.
In Column 15, line 51, "with  IN NaOH" should read
     --with  IN NaOH--.
In Column 15, line 60, "mercaptoe-" should read --mercapto- --.
In Column 15, line 61, "thylamine" should read --ethylamine--.
In Column 16, line 2, "IN sodium" should read --IN sodium--.
In Column 16, line 31, "IN NaOH" should read --IN NaOH--.
In Column 16, line 37, "0.005M" should read --0.05M--.
In Column 16, line 44, "0.1M KH₂PO₄pH7.0" should read
     --0.1M KH₂PO₄ pH7.0--.
```

In Column 17, line 8, "0.1M $KH_2PO_4$ 20mM" should read
--0.1$\underline{M}$ $KH_2PO_4$ 20$\underline{mM}$--.

Page 1 of 3

UNITED STATES PATENT AND TRADEMARK OFFICE
CERTIFICATE OF CORRECTION

PATENT NO. : 4,801,726
DATED : January 31, 1989
INVENTOR(S) : Roger W. Giese, et al.

It is certified that error appears in the above-identified patent and that said Letters Patent is hereby corrected as shown below:

In Column 18, line 10, "of 14C succinylated" should read --of $^{14}C$ succinylated--.

In Column 19, line 26, "actone" should read --acetone--.

In Column 19, line 56, "the T-2" should read --The T-2--.

In Column 21, line 37, "hit and run" should read --hit-and-run--.

In Column 25, line 13, "treated" should read --tested--.

In Column 26, line 46, "mercaptoethyla-" should read --mercaptoethyl-

In Column 26, line 47, "mine" should read --amine--.

In Column 26, line 64, "release" should read --releases--.

In Column 26, line 68, "sepharose 6b (pharmacia)" should read --Sepharose 6B (Pharmacia)--.

In Column 28, line 17, "Fab' through" should read --Fab' is reacted with nylon immobilized insulin by pumping [$^{125}I$] Fab' through--.

UNITED STATES PATENT AND TRADEMARK OFFICE
CERTIFICATE OF CORRECTION

PATENT NO. : 4,801,726

DATED : January 31, 1989

INVENTOR(S) : Roger W. Giese, et al.

It is certified that error appears in the above-identified patent and that said Letters Patent is hereby corrected as shown below:

In Column 29, line 3, "(diacetoxycrirpenol toxin)" should read
--(diacetoxyscrirpenol toxin)--.

Signed and Sealed this

Sixteenth Day of June, 1992

Attest:

DOUGLAS B. COMER

*Attesting Officer*   Acting Commissioner of Patents and Trademarks